United States Patent [19]

Nakane

[11] Patent Number: 4,638,012

[45] Date of Patent: Jan. 20, 1987

[54] 7-OXABICYCLOHEPTANE α-SUBSTITUTED KETONE PROSTAGLANDIN ANALOGS USEFUL IN THE TREATMENT OF THROMBOTIC DISEASE

[75] Inventor: Masami Nakane, Hopewell, N.J.

[73] Assignee: E. R. Squibb & Sons, Inc., Princeton, N.J.

[21] Appl. No.: 795,287

[22] Filed: Nov. 5, 1985

[51] Int. Cl.[4] .................. A61K 31/557; A61K 31/34; C07D 307/00

[52] U.S. Cl. ...................... 514/469; 549/463

[58] Field of Search .................... 549/463; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |
| 4,416,896 | 11/1983 | Nakane et al. | 549/463 |
| 4,456,617 | 6/1984 | Nakane et al. | 549/463 |

FOREIGN PATENT DOCUMENTS 0043292  8/1982  European Pat. Off. .
2039909  8/1980  United Kingdom .

*Primary Examiner*—Henry R. Jiles
*Assistant Examiner*—Bernard I. Dentz
*Attorney, Agent, or Firm*—Lawrence S. Levinson; Burton Rodney

[57] ABSTRACT

7-Oxabicycloheptane α-substituted ketone prostaglandin analogs are provided having the structural formula

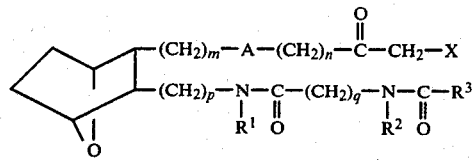

wherein m is 0 to 4; A is —CH=CH— or —CH$_2$—CH$_2$—; n is 1 to 5; X is halogen, alkanoyloxy or hydroxy; p is 1 to 4; R$^1$ is H or lower alkyl; q is 1 to 12; R$^2$ is H or lower alkyl; and R$^3$ is H, lower alkyl, lower alkenyl, lower alkynyl, aryl, arylalkyl, lower alkoxy, aryloxy, amino, alkylamino, or arylamino.

The compounds are cardiovascular agents useful, for example, in the treatment of thrombotic disease.

18 Claims, No Drawings

7-OXABICYCLOHEPTANE α-SUBSTITUTED KETONE PROSTAGLANDIN ANALOGS USEFUL IN THE TREATMENT OF THROMBOTIC DISEASE

DESCRIPTION OF THE INVENTION

The present invention relates to 7-oxabicycloheptane α-substituted ketone prostaglandin analogs which are cardiovascular agents useful, for example, in the treatment of thrombotic disease. These compounds have the structural formula

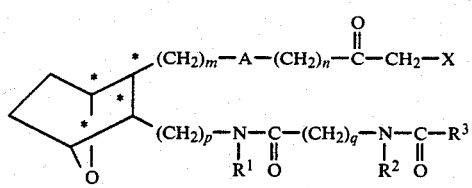

including all stereoisomers thereof, wherein m is 0 to 4; A is —CH=C— or —CH$_2$—CH$_2$—; n is 1 to 5; X is halogen, lower alkanoyloxy or hydroxy; p is 1 to 4; R$^1$ is H or lower alkyl; q is 1 to 12; R$^2$ is H or lower alkyl; and R$^3$ is H, lower alkyl, lower alkenyl, lower alkynyl, aryl, arylalkyl, lower alkoxy, aryloxy, amino, alkylamino, or arylamino.

The term "lower alkyl" or "alkyl" as employed herein alone or as part of another group includes both straight and branched chain hydrocarbon radicals containing 1 to 12 carbons such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as dwell as such groups including a halo-substituent, such as F, Br, Cl or I or CF$_3$, an alkoxy substituent, an aryl substituent, an alkyl-aryl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent, or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups 1 or 2 lower alkoxy groups. 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy" or "aralkoxy" as employed herein alone or as part of another group includes any of the above lower alkyl, alkyl or aralkyl groups linked to an oxygen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branchd chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The terms (CH$_2$)$_m$, (CH$_2$)$_n$ and (CH$_2$)$_p$ includes straight or branched chain radicals having from 0 to 4 carbons in the normal chain in the case of (CH$_2$)$_m$, from 1 to 5 carbons in the normal chain in the case of (CH$_2$)$_n$ and from 1 to 4 carbons in the normal chain in the case of (CH$_2$)$_p$ and may contain one or more lower alkyl and/or halogen substituents. Examples of (CH$_2$)$_m$, (CH$_2$)$_n$ and (CH$_2$)$_p$ groups include CH$_2$,

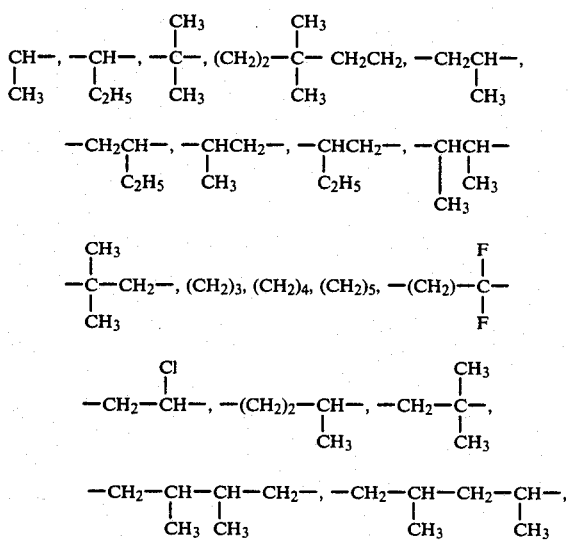

and the like.

The term (CH$_2$)$_q$ includes straight or branched chain radicals having from 1 to 12 carbons in the normal chain and includes any of the above examples of (CH$_2$)$_m$, (CH$_2$)$_n$ and (CH$_2$)$_p$ groups as well as (CH$_2$)$_6$, (CH$_2$)$_7$, (CH$_2$)$_8$, (CH$_2$)$_9$, (CH$_2$)$_{10}$, (CH$_2$)$_{11}$, (CH$_2$)$_{12}$, and may be substituted or substituted by one or more halo, hydroxy, alkoxy, amine, alkylamine, arylamine, amide, thioamide, thiol, alkylthio, arylthio, cyano or nitro groups.

The term "halogen" or "halo" as used herein refers to chlorine, bromine, fluorine, iodine and CF$_3$, with chlorine or fluorine being preferred.

Preferred are those compounds of formula I wherein m is 1 or 2, A is a —CH=CH—, n is 2 or 4, X is OH; p is 1, R$^1$ is H, (CH$_2$)$_q$ is —CH$_2$—; R$^2$ is H or CH$_3$, and R$^3$ is lower alkyl, such as pentyl, hexyl, or heptyl.

The compounds of formula I of the invention may be prepared as described below.

A. p is 1, m is 1, and R$^1$ is H

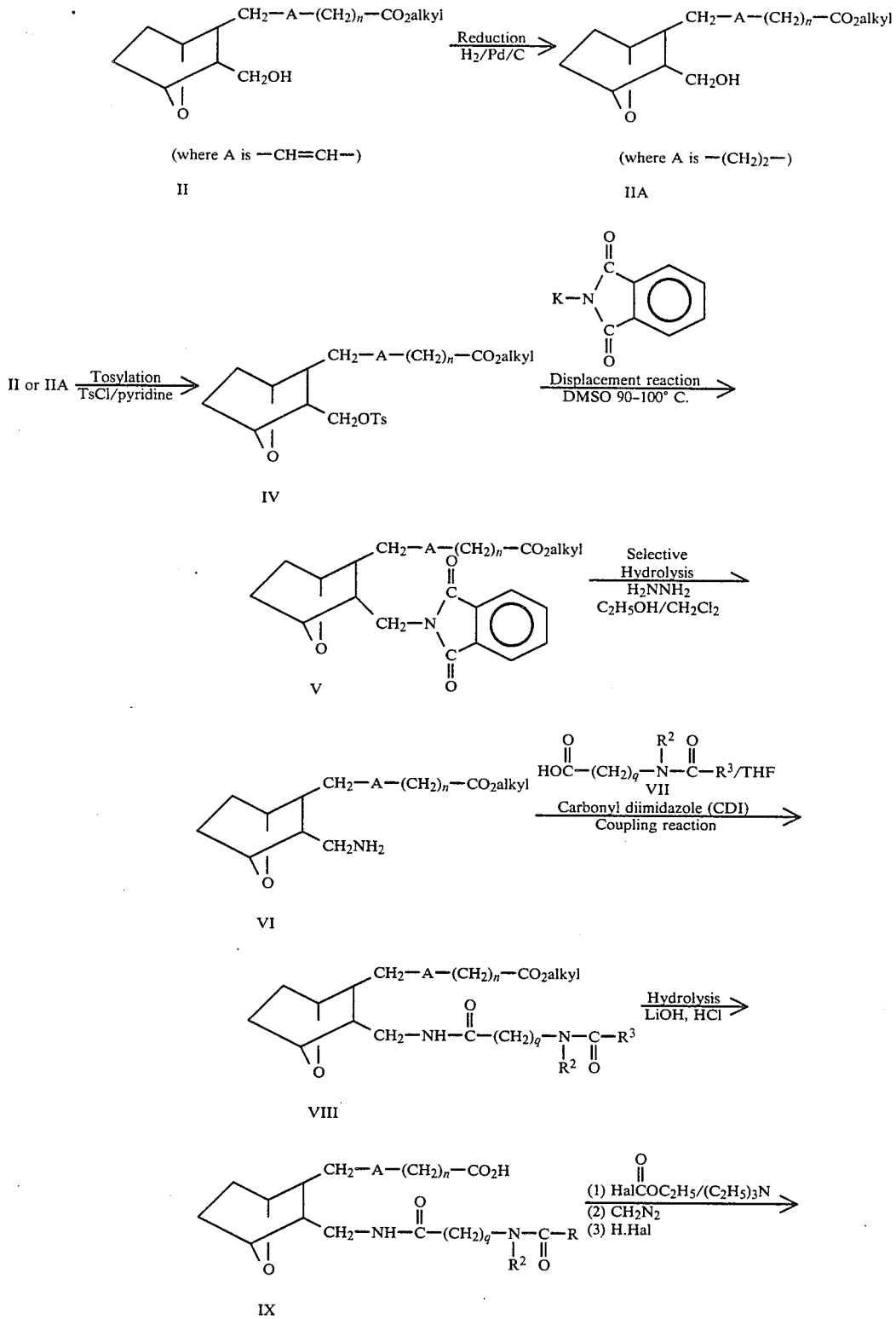

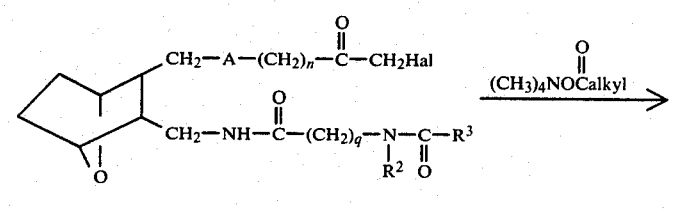
IA
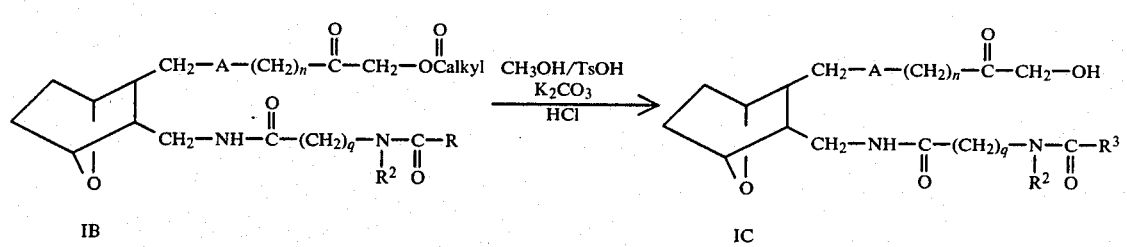
A'. Where p is 1, m is 1, and $R^1$ is alkyl
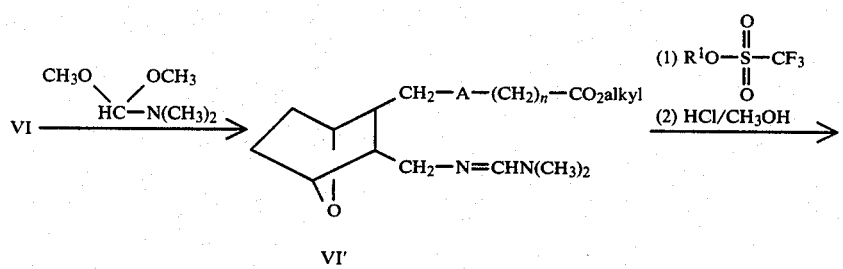
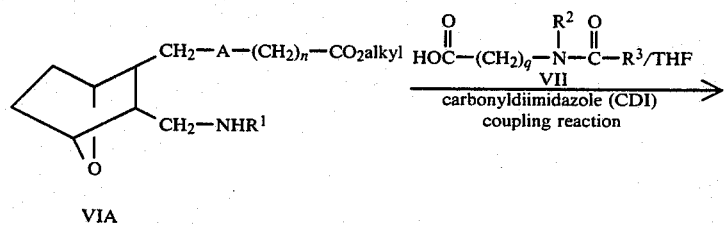
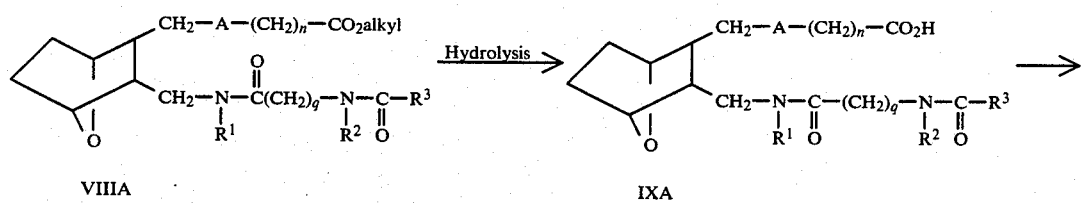
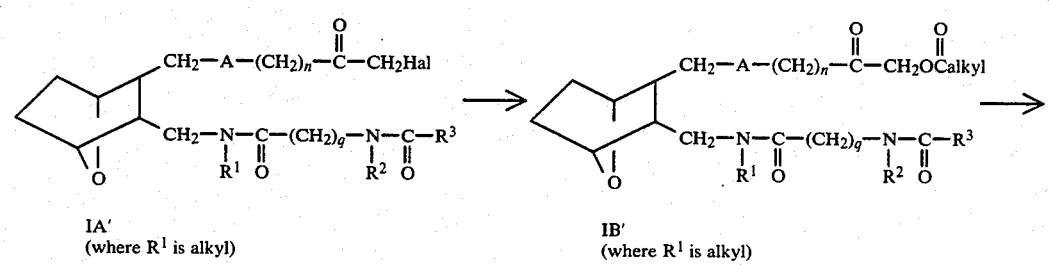
IA'
(where $R^1$ is alkyl)
IB'
(where $R^1$ is alkyl)

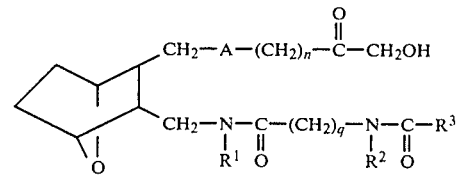
IC'
(where R¹ is alkyl)
B. Where p is 2 to 5, m is 1 and R¹ is H
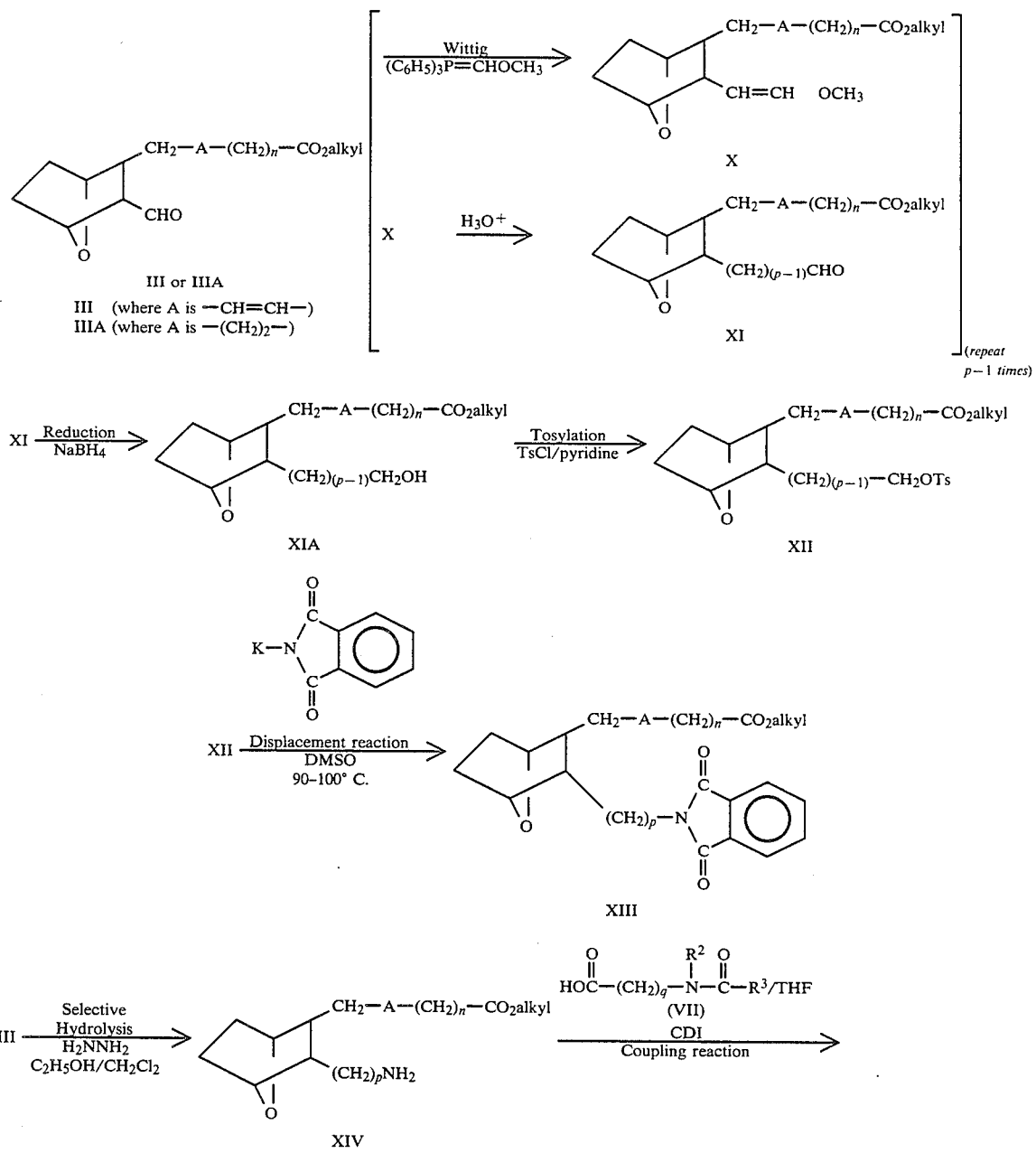

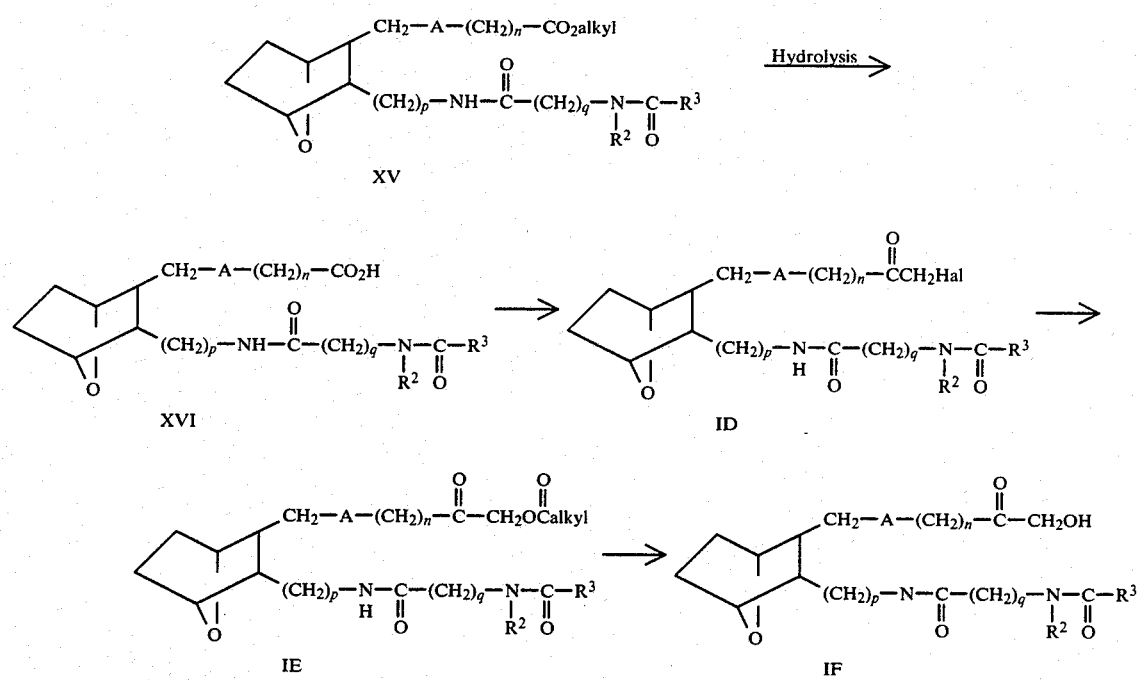
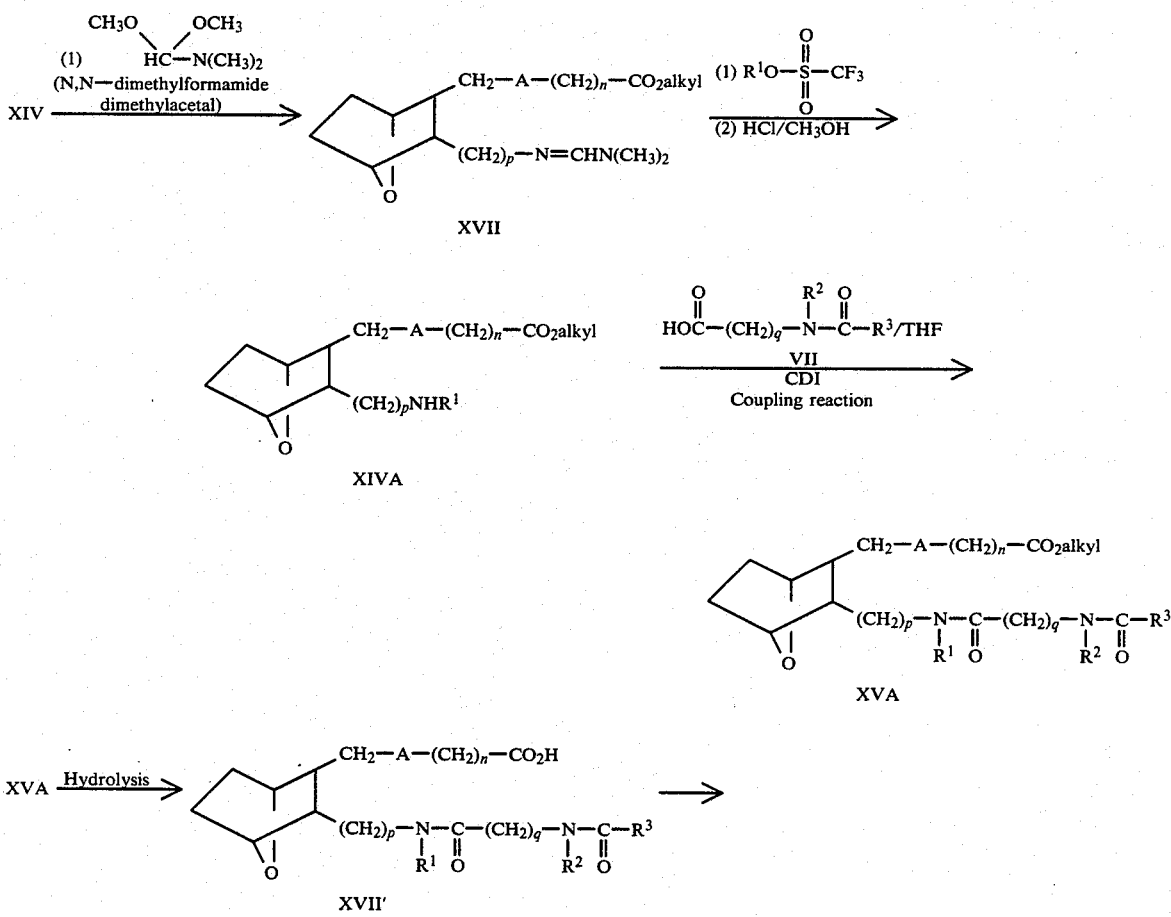
B'. Where p is 2 to 5, m is 1 and R¹ is alkyl

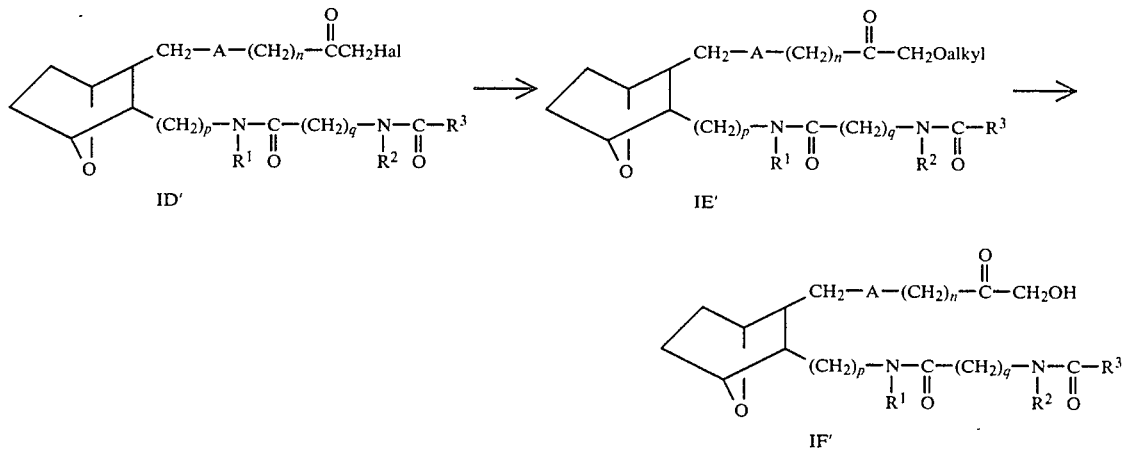
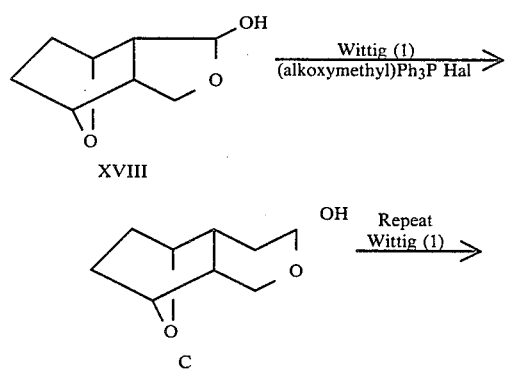
C. Where m is 2, p is 1, and A is —CH=CH—
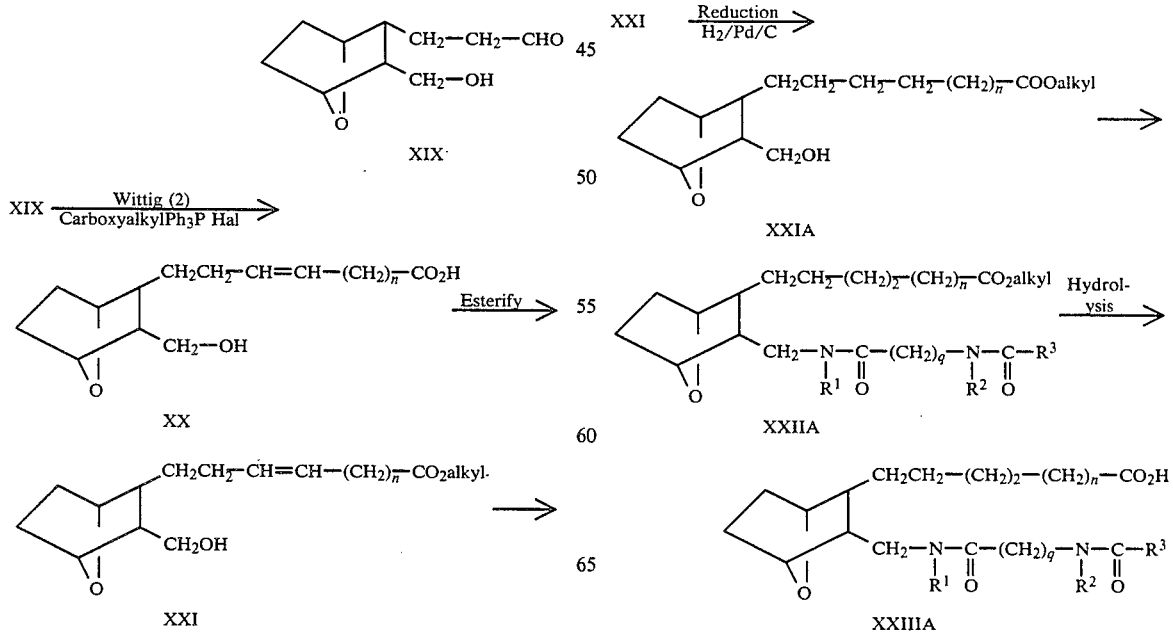

-continued

XXIIIA →(To final products, as per I, X = Hal)→ IJ

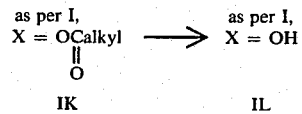
IK → IL

E. Where m is 3 or 4, p is 1, and A is —CH=CH—

XXIV →(Repeat Wittig (1) 1 time if m is 3 and 2 times if m is 4)→

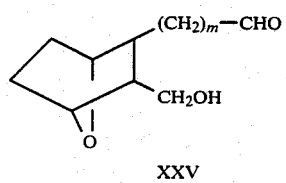
XXV →Wittig (2)→

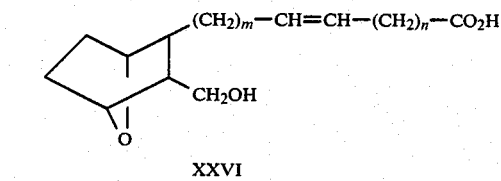
XXVI

XXVI →Esterification→

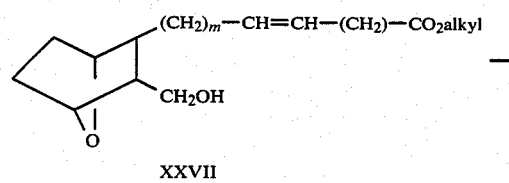
XXVII

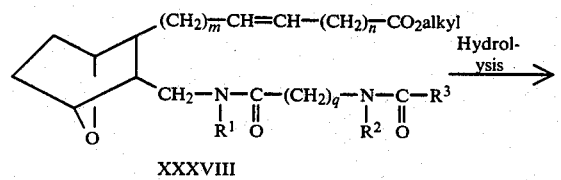
XXXVIII →Hydrolysis→

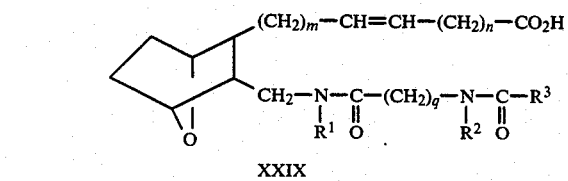
XXIX

XXIX →To final products, as per I, X = Hal→ IM

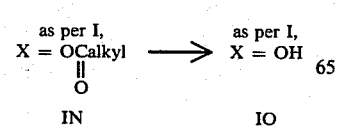
IN → IO

F. Where m is 3 or 4, p is 1, and A is $CH_2CH_2$

XXVII →Reduction $H_2$/Pd/C→

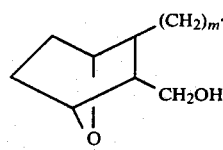
XXVIIA

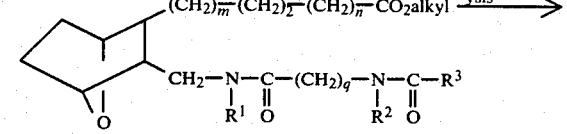
XXVIIIA →Hydrolysis→

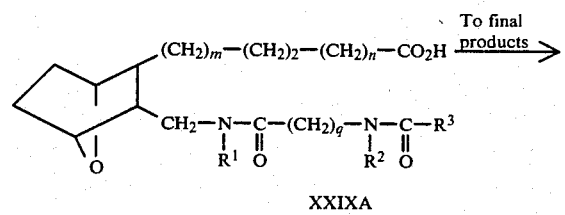
XXIXA →To final products→ as per I, X = Hal → as per I, X = OCalkyl → as per I, X = OH
IP              IQ                   IR G. Where m=0, A is —CH=CH—, and p is 1

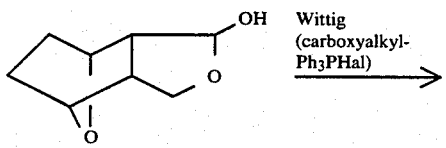
XVIII →Wittig (carboxyalkyl-$Ph_3$PHal)→

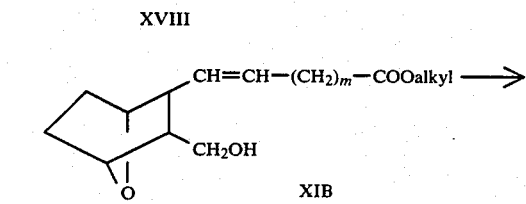
XIB

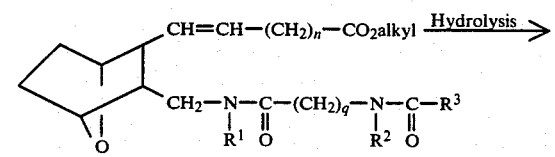
XXX →Hydrolysis→

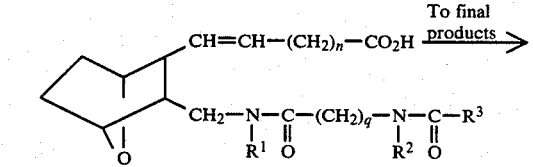
XXXI →To final products→

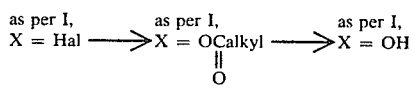

IS                      IU

H. Where m=0, A is —$(CH_2)_2$—, and p is 1

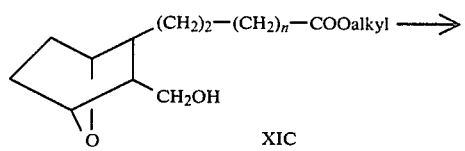

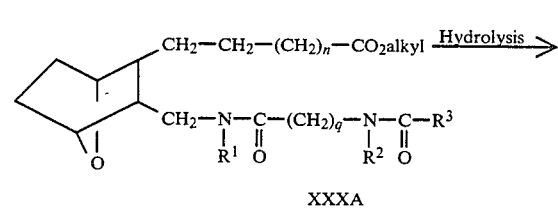

XXXA

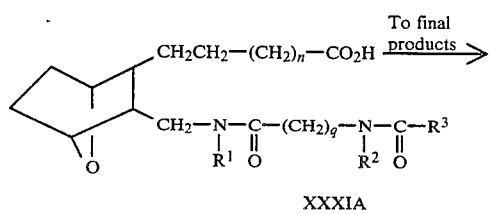

XXXIA

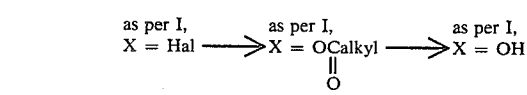

IV          IW          IY

I. Where $(CH_2)_n$ is

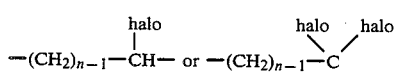

VIII,
VIIIA,
XV
XVA,
XXII,
XXIIA,     Ozonolysis / $O_3$ →
XXVIII,
XXVIIIA,
XXX,
XXXA

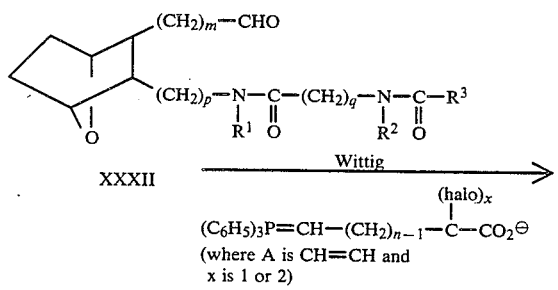

XXXII            Wittig →

$(C_6H_5)_3P=CH—(CH_2)_{n-1}—\overset{(halo)_x}{C}—CO_2^{\ominus}$ (where A is CH=CH and x is 1 or 2)

XXXIII as per I,      as per I,      as per I,
X = Hal → X = OCalkyl → X = OH
                    ‖
                    O

IZ           IAA           IBB

J. Where $R^3$ is $NH_2$

VI,
VIA  + $HO_2C—CH_2—NH—\overset{O}{\overset{\|}{C}}—NH_2$  (1) carbonyldiimidazole →
or XIV       (hydantoic acid)

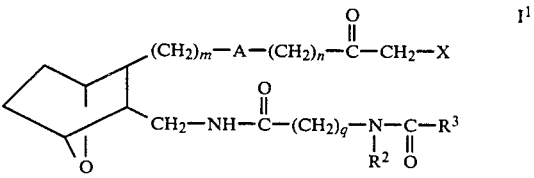

XXXIV

XXXV

ICC         IDD         IEE

As seen in reaction sequence "A", compounds of the invention where p is 1, and $R^1$ is H, that is $I^1$ are prepared by tosylating the lower alkyl ester containing the hydroxymethyl group, that is, compound II or IIA, (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

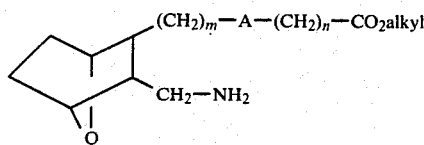
VI

As seen in reaction sequence "A'''", where $R^1$ is lower alkyl, an alkylation reaction is carried out as in the reference M. J. O'Donnell et al., Tetrahedron Lett. (1984), 25, 3651-3654 to give VIA

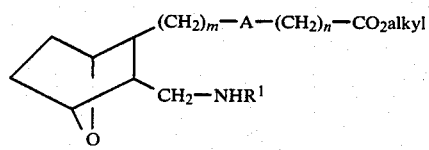
VIA

The amine VI or VIA is then subjected to a CDI coupling reaction by reacting VI or VIA with acid VII

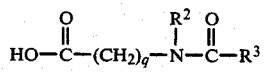
VII in the presence of an inert organic solvent such as tetrahydrofuran and carbonyl diimidazole under an inert atmosphere, such as argon, employing a molar ratio of VI:VII of within the range of from about 1:1 to about 1:1.2, to form the amide ester compound of the invention IA or IA'

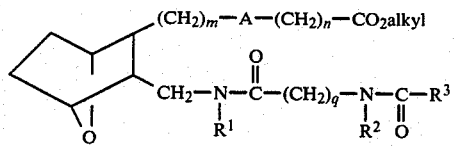

(VIII—where $R^1$ is H VIII'—where $R^1$ is lower alkyl)

The ester VIII or VIII' is then hydrolyzed by treating same with a base, such as lithium hydroxide, sodium hydroxide or potassium hydroxide to form the corresponding alkali metal salt, and the salt, without separating same from the reaction mixture, is neutralized with an acid, such as dilute hydrochloric acid or oxalic acid to form the acid IX or IXA. Acid IX or IXA is next treated with an alkyloxycarbonyl halide of the structure

A in the presence of an organic base (such as triethylamine), diazomethane and a strong acid such as hydrochloric acid to form the halomethyl carbonyl compound of the invention

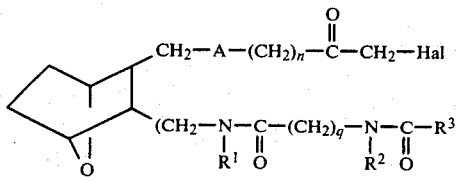

(IA—where $R^1$ is H IA'—where $R^1$ is alkyl)

Halomethylcarbonyl compound IA or IA' is then subjected to a displacement reaction wherein it is reacted with a compound of the structure B

B in acetonitrile to form the alkanoyloxymethylcarbonyl compound IB or IB' of the invention

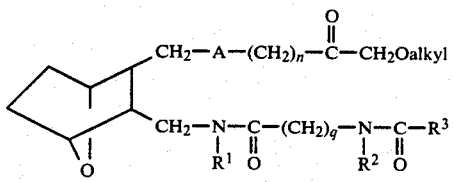

(IB where $R^1$ is H IB where $R^1$ is alkyl)

Compound IB or IB' is then subjected to a ketalization and hydrolysis wherein it is treated with p-toluenesulfonic acid in anhydrous methanol, weak base such as potassium carbonate is added and then recovered product is treated with hydrochloric acid to form hydroxymethylcarbonyl compound IC or IC'

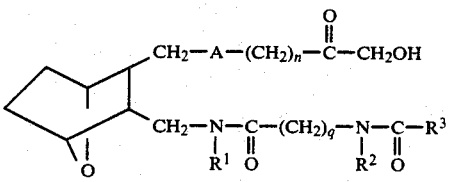

(IC where $R^1$ is H IC' where $R^1$ is alkyl)

The reaction sequences identified as "B" and "B'" are employed to prepare compounds of the invention wherein, p is 2 to 5, that is,

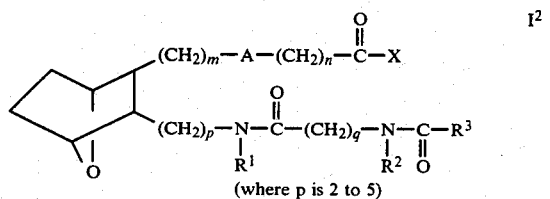
$I^2$
(where p is 2 to 5)

($I^{2a}$—where $R^1$ is H $I^{2b}$—where $R^1$ is alkyl)

Compound II or IIA is used to form the aldehyde III (where A is —CH=CH—) or IIIA (where A is —(CH$_2$)$_2$). Thus, to form aldehyde III where A is —CH=CH—, compound II is subjected to a Collins oxidation, for example, by reacting II with chromium trioxide in pyridine. To form the aldehyde IIIA (where A is (CH$_2$)$_2$) compound II is reduced, for example, with hydrogen over a palladium on carbon catalyst, to form hydroxymethyl compound IIA (where A is (CH₂)₂) and compound IIA is subjected to a Collins oxidation to form aldehyde IIIA (where A is (CH₂)₂). The aldehyde III or IIIA is used to prepare aldehyde XI where p is 2–5) by carrying out a homologation sequence, such as a Wittig reaction with (C₆H₅)₃P=CHOMe followed by hydrolysis, (P-1) times. The aldehyde XI (where p is 2–5) is then carried on to compounds of this invention where p is 2–5, that is

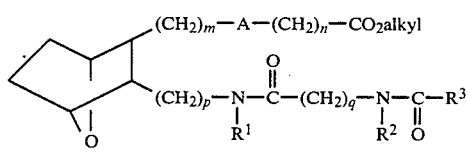 XV (where p is 2 to 5)
by reducing aldehyde XI by reacting with a reducing agent such as sodium borohydride to form alcohol XIA

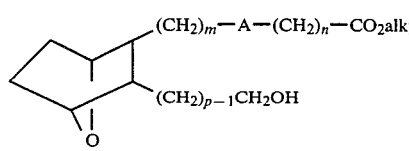 XIA tosylating alcohol XIA as described above to form the tosylate XII which is subjected to a displacement reaction with potassium phthalimide as described above to form the phthalimide XIII. Phthalimide XIII is then made to undergo selective hydrolysis as described above to form the amine XIV

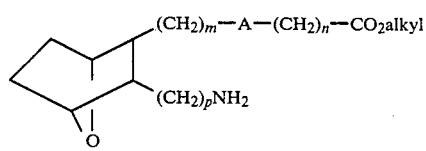 XIV

As seen in reaction sequence "B'", where R¹ is lower alkyl, an alkylation reaction is carried out as in O'Donnel et al, supra to give XIVA

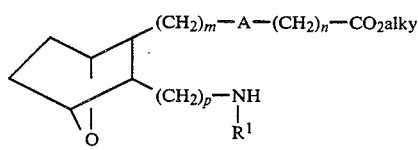 XIVA

The amine XIV or XIVA is then reacted with acid VII in a CDI coupling reaction as described above to form the amide ester compound of the invention XV or XVA

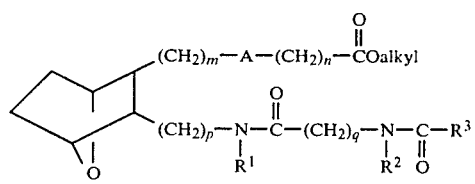

(XV—where R¹ is H  XVA—where R¹ is lower alkyl)

The ester XV or XVA is then hydrolyzed to the corresponding acid XVI or XVIA. Acid XVI or XVIA is then treated with alkoxycarbonyl halide A as described above to form the corresponding halomethylcarbonyl compound of the invention ID or ID' which is then made to undergo a displacement reaction wherein it is reacted with B as described above to form the alkanoyloxymethylcarbonyl compound IE or IE' of the invention. Compound IE or IE' is then subjected to ketalization and followed by base and then acid hydrolyses as described above to form hydroxymethylcarbonyl compound IF or IF'.

Compounds of the invention wherein m is 2, A is —CH=CH— and p is 1 may be prepared as outlined in reaction sequence "C" by subjecting starting compound XVII to a Wittig reaction, referred to as Wittig (1), by reacting XIII with an alkoxymethyltriphenyl phosphonium halide, such as (methoxymethyl)triphenylphosphonium chloride, for example, as described in Example 4 of U.S. Pat. No. 4,143,054, to form compound C. The Wittig (1) procedure is repeated on compound C to form aldehyde compound XIX. Aldehyde XIX is then subjected to a Wittig (2) procedure wherein XIX is reacted with a carboxyalkyltriphenylphosphonium halide, such as carboxypentyltriphenylphosphonium bromide, to form hydroxymethyl compound XX. Compound XX is esterified, for example, by reacting with diazomethane, to form ester XXI which is then employed in place of compound IX in reaction scheme "A" to form compounds IG, IH and II of the invention.

As seen in reaction sequence "D", compounds of the invention wherein m is 2, A is —CH₂—CH₂—, and p is 1 may be prepared as outlined in reaction sequence "D" by reducing hydroxymethyl compound XXI to form compound XXIA which is then employed in place of compound IIA in reaction sequence "A" to form compounds IJ, IK and IL of the invention.

Referring to reaction sequence "E", compounds of the invention wherein m is 3 or 4, A is —CH=CH—, and p is 1 and may be prepared by subjecting aldehyde XXIV to the Wittig (1) procedure one time in the case where m is 3 and a second time in the case where m is 4, to form the aldehyde XXV. Aldehyde XXV is then subjected to the Wittig (2) procedure to form acid XXVI which is esterified to form ester XXVII which is then employed in place of compound II in reaction scheme "A" to form compounds IM, IN and IO of the invention.

As seen in reaction sequence "F", compounds of the invention wherein m is 3 or 4, A is CH₂CH₂, and p is 1 and may be prepared by reducing hydroxymethyl compound XXVII to form compound XXVIIA which is then employed in place of compound II in reaction scheme "A" to form compounds IP, IQ and IR of the invention.

Thus, compounds of the invention wherein m is 0, 2, 3 or 4 and p is 2, 3 or 4 may be prepared by substituting hydroxymethyl compound XXI, XXIA, XXVII or XXVIIA in place of hydroxymethyl compound II or IIA in reaction sequences A and B.

Referring now to reaction sequence "G", compounds of the invention wherein m is 0, A is CH=CH and p is 1, that is, compounds IS, IT and IU may be prepared by subjecting compound XVII (prepared as described in Example 3 of U.S. Pat. No. 4,143,054) to a Wittig reaction, for example, as described in Example 6(c) of U.S. Pat. No. 4,143,054, by reacting XVIII with a carboxyalkyltriphenyl phosphonium halide, such as carboxypentyltriphenyl phosphonium bromide to form the hydroxymethyl compound XIB which may then be used to form the ester XXX which, in turn, may be hydrolyzed to the corresponding acid XXXI and then employed in place of acid IX or IXA in reaction schemes A and B to form compounds of the invention IS, IT and IU.

As seen in reaction sequence "H", where it is desired to prepare compounds of the invention wherein m is 0 and A is $(CH_2)_2$, the hydroxymethyl compound XIB is reduced by treatment with hydrogen in the presence of a palladium on carbon catalyst to form hydroxymethyl compound XIC which may then be used to form ester XXXA. Ester XXXA then may be hydrolyzed to the corresponding acid XXXIA which is used in place of acid IX and IXB in reaction schemes A and B to form compounds of the invention IV, IW, and IY.

Referring to reaction sequence "I", compounds of formula I of the invention wherein

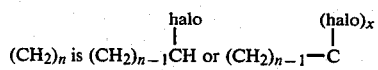

where x is 2
may be prepared by subjecting ester VIII, VIIIA, XV, XVA, XXII, XXIIA, XXVIII, XXVIIIA, XXX and XXXA to ozonolysis by treating these esters with ozone at −78° C. in methylene chloride and methanol to form aldehyde XXXII.

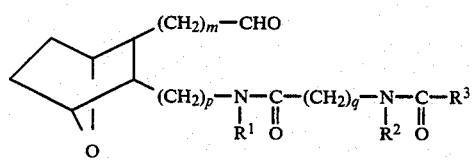

XXXII which is then treated with Wittig reagent

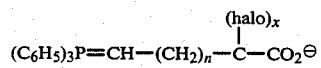

D (where A is CH=CH and x is 1 or 2)
to form acid compound XXXIII. Acid XXXIII is then used in place of acid IX or IXB in reaction schemes A and B to form compounds IZ, IAA and IBB of the invention.

In reaction sequence "J" compounds of the invention wherein $R^3$ is $NH_2$, that is IT

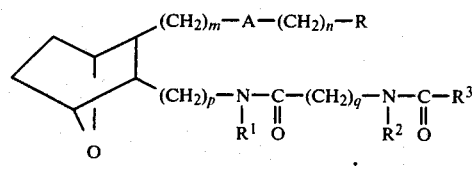

IT may be prepared by reacting amine VI, VIA or XIV with hydantoic acid in the presence of carbonyldiimidazole and then hydrolyzing the resulting product to form ester XXXIV which is then used in place of ester VIII or VIIIA in reaction sequence A or B to form compounds of the invention ICC, IDD or IEE.

The starting acid VII

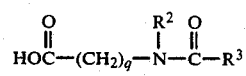

VII may be prepared by reacting the amino acid J

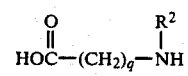

J with acid chloride K

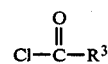

K in the presence of a strong base such as NaOH and water.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cisendo and all trans forms and stereoisomeric pairs may be prepared as shown in the working Examples which follow and by employing starting materials following the procedures as outlined in U.S. Pat. No. 4,143,054. Examples of such stereoisomers are set out below.

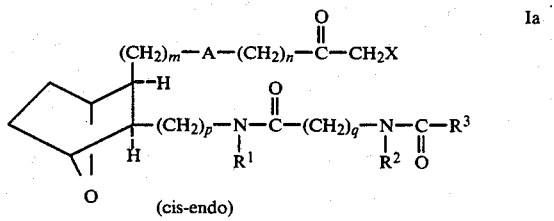

Ia (cis-endo)

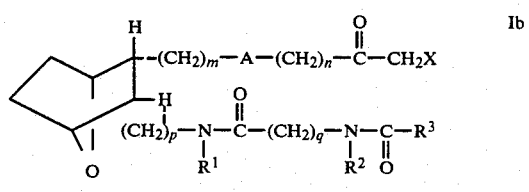

Ib (cis-exo)

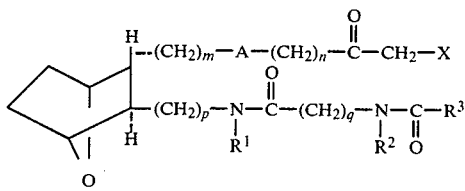

(trans)

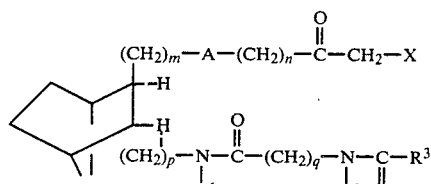

(trans)

The nucleus in each of the compounds of the invention is depicted as

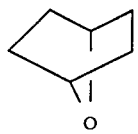

for matter of convenience; it will also be appreciated that the nucleus in the compounds of the invention may be depicted as

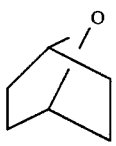

The compounds of this invention are cardio-vascular agents useful as platelet aggregation inhibitors, such as in inhibiting arachidonic acid-induced platelet aggregation, e.g., for treatment of thrombotic disease such as coronary or cerebral thromboses, and in inhibiting broncho-constriction. They are also selective thromboxane A$_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 0.1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1S-[1β,2α(5Z),3α,4β]]-1-Chloro-8-[3-[[[[(1-oxohexyl)amino]acetyl]amino]methyl]-7-oxabicyclo[2.2.1]hept-2-yl]-6-octen-2-one

A. N-Hexanoylglycine

Glycine (7.5 g, 100 mmol) was dissolved in NaOH solution (NaOH:8 g, H$_2$O:50 ml) and cooled to 0° C. Et$_2$O (50 ml) was added and n-hexanoyl chloride (13.4 g, 100 mmol) was then added dropwise over 60 minutes at 0° C. under vigorous stirring. The reaction was allowed to warm to rom temperature and was stirred for 1 hour. 1N-NaOH (10 ml) was added and the layers were separated. The water layer was washed with Et$_2$O (20 ml×2). The combined Et$_2$O layers were extracted with 1N-NaOH (20 ml). The combined water layers were acidified with concentrated HCl to pH 2 and the products were extracted with Et$_2$O (100 ml×3). The combined Et$_2$O layers were washed with brine (50 ml) and dried over MgSO$_4$. Filtration and evaporation of solvent gave a colorless solid (16.2 g), which was crystallized from EtOAc (60 ml) to give colorless needle crystals (10.9 g, 63 mmol, 63%), m.p. 93°–96°. TLC: silica gel, MeOH, CH$_2$Cl$_2$, HCOOH; 10, 89.5, 0.5, PMA R$_f$=0.45.

B. [1S-[1β,2α(5Z),3α,4β]]-7-[3-(Tosyloxymethyl)-7-oxabicyclo[2.2.1]hept-2-yl]-5-heptenoic acid, methyl ester Tosyl chloride (4.256 g, 22.4 mmol) dissolved in CH$_2$Cl$_2$ (30 ml) was added dropwise to a magnetically stirred solution of [1S-[1β,2α(5Z),3α,4β]]-7-[3-(hydroxymethyl)-7-oxabicyclo[2.2.1]hept-2-yl]-5-heptenoic acid, methyl ester (prepared as described in U.S. Pat. No. 4,143,054 (3 g, 11.2 mmol) in pyridine (30 ml) at 0° C. After completion of the addition, the reaction was warmed to room temperature and stirred overnight. The reaction was poured into ice/H$_2$O and stirred for 30 minutes. The products were extracted with EtOAc (80 ml×3). The combined EtOAc layers were washed with 3N-HCl (40 ml×3), saturated NaHCO$_3$, brine and dried over MgSO$_4$. Filtration and evaporation of solvent gave a white solid, which was crystallized from isopropyl ether to give the corresponding title tosylate in the form of needle crystals (4.23 g, 89% ), m.p. 68°–70° C.

C. [1S-[1,2α(5Z),3α,4β]]-7-[(3-Aminomethyl)-7-oxabicyclo[2.2.1]hept-2-yl]-5-heptenoic acid, methyl ester The title B tosylate was subjected to a Gabriel synthesis to form the corresponding amino compound as described below.

The potassium phthalimide used was purified prior to use by boiling 5 g thereof with 9 ml acetone for 15 minutes, filtering while hot and washing with 5 ml acetone. The remaining solid was dried in vacuo for 6 hours at 100° C. prior to use.

The title B tosylate (8.11 g, 19.2 mmol) and purified potassium phthalimide (6.4 g, 34.6 mmol, 1.8 equiv.) in dimethylsulfoxide (70 ml, Burdick & Jackson) were heated at 90°-100° C. for 2½ hours (checked by TLC Et$_2$O-pet ether 2:1, no tosylate remaining). After cooling to room temperature, water (90 ml) was added. Material began precipitating. The mixture was poured into ice water (~350 ml) and stirred 30 minutes. The straw colored solid was harvested by filtration and washed with more water. The solid was dissolved in warm ethyl acetate (150 ml), washed with water (3×50 ml), dried (MgSO$_4$), filtered and freed of solvent in vacuo. The remaining solid (7.88 g) was recrystallized from isopropyl ether (~150 ml) to give corresponding phthalimide (6.35 g, 83%) TLC. Et$_2$O-hexane 2:1, UV+vanillin R$_f$=0.38, trace 0.09.

The above phthalimide (5.05 g, 13.8 mmol) was dissolved in distilled CH$_2$Cl$_2$ (24 ml) and distilled ethanol (104 ml) in an argon atmosphere. Anhydrous hydrazine (0.78 ml, 25.6 mmol) was added. The mixture was stirred at room temperature. After 8 hours an additional 0.2 ml of hydrazine was added and the mixture was stirred an additional 15 hours at room temperature. A white solid was removed by filtration and washed with more CH$_2$Cl$_2$. The filtrate was taken to dryness in vacuo (on the pump at end). Cold 0.5N HCl solution (80 ml) was added. A small amount of white solid was removed by filtration and washed with additional 0.5N HCl solution (80 ml). The acidic solution was washed with ether (2×100 ml) and then basified with solid K$_2$CO$_3$. The amine was extracted into CHCl$_3$ (3×100 ml), dried (MgSO$_4$) and freed of solvent in vacuo leaving a yellow oil. Ether (100 ml) was added to this oil. Some solid was insoluble. After cooling in an ice bath, the solid was removed by filtration. The solvent was removed from the filtrate in vacuo leaving title amine as a pale yellow oil (2.441 g, 71%). NMR spectra and TLC indicated some minor impurities. The material was used without further purification.

D.
[1S-[1β,2α(5Z),3α,4β]]-7-[3-[[[[(1-Oxohexyl)amino]acetyl]amino]methyl]-7-oxabicyclo[2.2.1]hept-2-yl]-5-heptenoic acid, methyl ester Part A compound (260 mg, 1.5 mmol) was dissolved in distilled THF (12 ml) in an argon atmosphere. After cooling in an ice bath carbonyldiimidazole (CDI) (243 mg, 1.5 mmol) was added. The mixture was stirred cold for 1 hour and then at room temperature for 1 hour. The solution was cooled to 0° C. and a solution of Part C amine (401 mg, 1.5 mmol) in THF (3 ml) was added. The mixture was left stirring overnight at room temperature. The solvent was removed in vacuo and the residue was dissolved in CHCl$_3$ (50 ml). This was washed with 1N HCl (20 ml), 1N NaOH (20 ml) and H$_2$O (20 ml), dried (MgSO$_4$) and freed of solvent in vacuo leaving a viscous oil. The oil was chromatographed on silica gel (30 g, Baker for flash chromatography), eluting with EtOAc and 1% MeOH in EtOAc to give title compound as an oil (425 mg, 67%). TLC: silica gel, 10% MeOH in CH$_2$Cl$_2$, vanillin R$_f$=0.48.

E.
[1S-[1β,2α(5Z),3α,4β]]-7-[3-[[[[(1-Oxohexyl)amino]acetyl]amino]methyl]-7-oxabicyclo[2.2.1]hept-2-yl]-5-heptenoic acid.

The Part D methyl ester (420 mg, 0.994 mmol) was dissolved in distilled THF (40 ml) and water (8 ml) in an argon atomsphere. 1N LiOH solution (9.5 ml) was added and the mixture was stirred at room temperature for 3¾ hours. After neutralization with 1N HCl (9.5 ml), solid KCl was added and the layers were separated. The aqueous layer was reextracted with CHCl$_3$ (3×50 ml). The combined organic layers (THF+CHCl$_3$) were washed with saturated NaCl solution (2×25 ml), dried (MgSO$_4$), and freed of solvent in vacuo leaving a very viscous oil. This was chromatographed on silica gel (30 g, Baker for flash chromatography) eluting with 4% MeOH in CH$_2$Cl$_2$ to give material which crystallized, (358 mg, 88%). This was recrystallized from acetonitrile (~10 ml) to give title acid, 248 mg, 61%, m.p. 119°-121° C.). TLC: silica gel, 10% MeOH in CH$_2$Cl$_2$, vanillin, R$_f$=0.37.

Anal Calcd for C$_{22}$H$_{36}$O$_5$N$_2$: C, 64.68; H, 8.88; N, 6.86; Found: C, 64.67; H, 8.87; N, 6.86.

F.
[1S-[1β,2α(5Z),3α,4β]]-1-Chloro-8-[3-[[[[(1-oxohexyl)amino]acetyl]amino]-methyl]-7-oxabicyclo[2.2.1]hept-2-yl]-6-octen-2-one

(119.4 mg) is added dropwise to a magnetically stirred solution of Part D [1S-[1β,2α(5Z),3α,4β]]-7-[3-[[[[(1-oxohexyl)amino]-acetyl]amino]methyl-7-oxabicyclo[2.2.1]hept-2-yl]-5-heptenoic acid (408 mg) and Et$_3$N (121.2 mg) in THF (10 ml) at 0° C. and the reaction is stirred for 1 hour. CH$_2$N$_2$ solution in Et$_2$O (CH$_2$N$_2$:~2 mmol) is added at 0° C. and the rection is allowed to warm to room temperature. After stirring overnight (15 hours), the reaction is cooled to 0° C. and HCl gas is introduced until N$_2$ evolution no longer takes place. The reaction is warmed to room temperature and stirred for 1 hour. The reaction is poured into EtOAc (80 ml) and washed with saturated NaHCO$_3$ (20 ml). The water layer is reextracted with EtOAc (80 ml). The combined organic layers are washed with H$_2$O (30 ml×2) and dried over MgSO$_4$. Filtration and evaporation of solvents give a crude product which is purified by silica gel column. The title compound is thus obtained.

EXAMPLE 2
[1S-[1β,2α(5Z),3α,4β]]-1-Acetoxy-8-[3-[[[[(1-oxohexyl)amino]acetyl]amino]methyl]-7-oxabicyclo[2.2.1]hept-2-yl]-6-octen-2-one (CH$_3$)$_4$NOAc (252 mg, 1.896 mmol) is added to a magnetically stirred solution of chloride prepared in Example 1 (723 mg, 1.58 mmol) in CH$_3$CN (15 ml) at room temperature. Stirring is continued overnight (14 hours) at room temperature. The reaction is concentrated in vacuo. The residue is partitioned between H$_2$O (30 ml) and EtOAc (80 ml). The EtOAc layer is washed with H$_2$O (20 ml) and dried over MgSO$_4$. Filtration and evaporation of solvent give a crude product which is purified by silica gel column. The title compound is obtained.

EXAMPLE 3

[1S-[1β,2α(5Z),3α,4β]]-Hydroxy-8-[3-[[[[(1-oxohexyl)amino]acetyl]amino]methyl]-7-oxabicyclo[2.2.1]hept-2-yl]-6-octen-2-one p-TsOH (10 mg, monohydrate) is added to acetate prepared in Example 2 (103 mg) in anhydrous MeOH (10 ml) at room temperature, and the reaction is stirred at room temperature for 20 hours. $K_2CO_3$ (anhydrous, 120 mg) is added and stirring is continued for 24 hours at room temperature. Saturated $NH_4Cl$ (20 ml) is added and the products are extracted with EtOAc (50 ml×2). The combined EtOAc layers are washed with brine (10 ml×2) and dried over $MgSO_4$. Filtration and evaporation of solvent give a crude product which is dissolved in THF (4 ml) and treated with 1N-HCl (4 ml). After 30 minutes of stirring at room temperature, the reaction is basified with saturated $NaHCO_3$ and the products are extracted with EtOAc (50 ml×2). The combined EtOAc layers are washed with brine (10 ml×2) and dried over $MgSO_4$. Filtration and evaporation of solvent give a crude product which is purified by silica gel column. The title compound is thus obtained.

EXAMPLE 5

[1S-[1β,2α(5Z),3α,4β]]-1-Chloro-8-[3-[[[[(Butylamino)carbonyl]amino]acetyl]amino]methyl]-7-oxabicyclo[2.2.1]hept-2-yl]-6-octen-2-one

A. N-[(Butylamino)carbonyl]glycine, ethyl ester

Glycine ether ester.HCl (5.58 g, 40 mmol) was suspended in distilled $CH_2Cl_2$ (20 ml). After cooling in an ice bath, distilled $Et_3N$ (6.13 ml, 44 mmol) was added. Distilled n-butyl isocyanate (4.95 ml, 44 mmol) was added. The cooling bath was removed and the mixture was left stirring overnight at room temperature. Additional $Et_3N$ (3.05 ml) was added and the mixture was stirred 3 more hours. After diluting with more $CH_2Cl_2$, the solution was washed with water (50 ml), 1N HCl (50 ml), saturated $NaHCO_3$ solution (50 ml) and water (50 ml). After drying ($MgSO_4$), the solvent was removed in vacuo leaving the title compound (7.641 g, 94%) which slowly crystallized. This was used without further purification.

B. N-[(Butylamino)carbonyl]glycine

Part A ethyl ester (3.378 g, 16.7 mmol) was dissolved in distilled THF (100 ml) and treated with 1N LiOH solution (40 ml). After stirring overnight at room temperature and acidifying with concentrated HCl, solid KCl was added. The layers were separated. The aqueous layer was reextracted with EtOAc (3×50 ml). The combined organic layers (THF and EtOAc) were washed with saturated NaCl solution (25 ml), dried ($MgSO_4$), and freed of solvent in vacuo leaving the title compound, as a white solid (2.81 g, 97%).

C. [1S-[1β,2α(5Z),3α,4β]]-7-[3-[[[[(Butylamino)carbonyl]amino]acetyl]amino]methyl]-7-oxabicyclo[2.2.1]hept-2-yl]-5-heptenoic acid, methyl ester Part B compound (174.2 mg, 1 mmol) was partially dissolved in distilled THF (8 ml) in an argon atmosphere. After cooling in an ice bath, carbonyl diimidazole (CDI) (162 mg, 1 mmol) was added. The mixture was stirred cold 1 hour and at room temperature 1½ hours (became a clear solution near the end of this time). The solution was cooled in an ice bath and a solution of chiral amine prepared in Example 1 Part C (267 mg, 1 mmol) in THF (3 ml) was added. The cooling bath was removed and the mixture was left stirring overnight at room temperature. The solvent was removed in vacuo. $CHCl_3$ (35 ml) was added to the residue. The solution was washed with 1N HCl (15 ml), 1N NaOH (15 ml) and $H_2O$ (15 ml), dried ($MgSO_4$) and freed of solvent in vacuo leaving a very viscous oil (340 mg). This was chromatographed on silica gel (20 g, Baker for flash chromatography), eluting with EtOAc and 5% MeOH in EtOAc to give the title compound as a viscous oil (212 mg, 50%). TLC: silica gel, 5% MeOH in EtOAc, vanillin, $R_f=0.23$.

D. [1S-[1β,2α(5Z),3α,4β]]-7-[3-[[[[(Butylamino)carbonyl]amino]acetyl]amino]methyl]-7-oxabicyclo[2.2.1]hept-2-yl]-5-heptenoic acid Part C methyl ester (208 mg, 0.491 mmol) was dissolved in distilled THF (20 ml) and water (4.8 ml) in an argon atmosphere. 1N LiOH solution (4.9 ml) was added and the mixture was stirred at room temperature 5 hours. The mixture was neutralized with 1N HCl solution (4.9 ml) and solid KCl was added. The layers were separated. The aqueous layer was reextracted with $CHCl_3$ (3×25 ml). The combined organic layers (THF and $CHCl_3$) were washed with saturated NaCl solution (15 ml), dried ($MgSO_4$) and freed of solvent in vacuo leaving an oil. This was chromatographed on silica gel (18 g), eluting with 4% MeOH in $CH_2Cl_2$ to give the title compound (158 mg, 78.2%) as a white foam. TLC: silica gel, 10% MeOH in $CH_2Cl_2$, vanillin, $R_f=0.28$.

Anal Calcd for $C_{21}H_{35}O_5N_3.0.1H_2O$: C, 61.32; H, 8.63; N, 10.21; Found: C, 61.15; H, 8.74; N, 10.23.

E. [1S-[1β,2α(5Z),3α,4β]]-1-Chloro-[3-[[[[(Butylamino)carbonyl]amino]acetyl]amino]methyl]-7-oxabicyclo[2.2.1]hept-2-yl]-6-octen-2-one Following the procedure of Example 1 Part F except substituting the above Part D acid for the Example 1 Part E acid, the title compound is obtained.

EXAMPLE 6

[1S-[1β,2α(5Z),3α,4β]]-1-Acetoxy-8-[3-[[[[(butylamino)carbonyl]amino]acetyl]amino]methyl]-7-oxabicyclo[2.2.1]hept-2-yl]-6-octen-2-one Following the procedure of Example 2 except substituting the Example 5 compound for the Example 1 compound, the title compound is obtained.

EXAMPLE 7

[1S-[1β,2α(5Z),3α,4β]]-1-Hydroxy-8-[3-[[[[(butylamino)carbonyl]amino]acetyl]amino]methyl]-7-oxabicyclo[2.2.1]hept-2-yl]-6-octen-2-one Following the procedure of Example 3 except substituting the Example 6 compound for the Example 2 compound, the title compound is obtained.

EXAMPLE 8

[1S-[1β,2α(5Z),3α,4β]]-1-Chloro-8-[3-[[[[Methyl(1-oxohexyl)amino]acetyl]amino]methyl]-7-oxabicyclo[2.2.1]hept-2-yl]-6-octen-2-one acid

A. N-hexanoyl-N-methylglycine

Sarcosine (1.78 g, 20 mmol) was dissolved in 1N NaOH solution (40 ml) and Et$_2$O (40 ml) was added. After cooling in an ice bath a solution of hexanoyl chloride (3.1 ml, 22 mmol) in Et$_2$O (10 ml) was added dropwise. The mixture was stirred cold for 1 hour. The pH was then adjusted to about 8 by adding 1N NaOH solution (about 3 ml) and the mixture was stirred at room temperature 45 minutes. NaOH solution was added to about pH 9-10. The layers were separated and the aqueous layer was washed with Et$_2$O (50 ml). After acidification of the aqueous layer with concentrated HCl and saturation with solid KCl, the product was extracted into CHCl$_3$ (3×70 ml). The combined CHCl$_3$ extracts were washed with saturated NaCl solution (25 ml), dried (MgSO$_4$), and freed of solvent leaving the title compound as an oil (3.78 g, quant.) which was used without further purification.

B.
[1S-[1β,2α(5Z),3α,4β]]-7-[3-[[[[Methyl(1-oxohexyl)amino]acetyl]amino]methyl]-7-oxabicyclo[2.2.1]hept-2-yl]-5-heptenoic acid, methyl ester Part A compound (187 mg, 1 mmol) was dissolved in distilled THF (8 ml) in an argon atmosphere and cooled in an ice bath. Carbonyldiimidazole (CDI) (162 mg, 1 mmol) was added and the mixture was stirred cold for 1 hour and then for 1 hour at room temperature. After cooling in an ice bath, a solution of chiral amine prepared in Example 1 part C (267 mg, 1 mmol) in THF (3 ml) was added. The ice bath was removed and the mixture was stirred overnight at room temperature. The solvent was removed in vacuo. CHCl$_3$ (35 ml) was added to the residue. The solution was washed with 1N HCl (15 ml), 1N NaOH solution (15 ml) and H$_2$O (15 ml), dried (MgSO$_4$) and freed of solvent in vacuo leaving an oil (424 mg). This was chromatographed on silica gel (20 g, Baker for flash chromatography), eluting with EtOAc and 2% MeOH in EtOAc to give the title compound as an oil (252 mg, 57.7%). TLC: silica gel, 5% MeOH in EtOAc, vanillin; R$_f$=0.46.

C.
[1S-[1β,2α(5Z),3α,4β]]-7-[3-[[[[Methyl(1-oxohexyl)amino]acetyl]amino]methy]-7oxabicyclo[2.2.1]hept-2-yl]-5-heptenoic acid The part B methyl ester (248 mg, 0.568 mmol) was dissolved in distilled THF (25 ml) and water (5 ml) in an argon atmosphere. 1N LiOH solution was added and the mixture was stirred at room temperature 4 hours. After neutralizing with 1N HCl solution (5.6 ml) and addition of solid KCl, the layers were separated. The aqueous layer was extracted with CHCl$_3$ (3×25 ml). The combined organic layers (THF+CHCl$_3$) were washed with saturated NaCl solution (15 ml), dried (MgSO$_4$) and freed of solvent in vacuo leaving an oil (242 mg). This was chromatographed on silica gel (20 g, Baker for flash chromatography) eluting with 4% MeOH in CH$_2$Cl$_2$ to give the title compound (191.8 mg, 79.9%) as a viscous oil. TLC: silica gel; 10% MeOH in CH$_2$Cl$_2$, vanillin, R$_f$=0.46.

Anal Calcd for C$_{23}$H$_{38}$O$_5$N$_2$; C, 65.37; H, 9.06 N, 6.63; Found: C, 65.50; H, 9.10; N, 6.74.

D.
[1S-[1β,2α(5Z),3α,4β]]-1-Chloro-8-[3-[[[[Methyl(1-oxohexyl)amino]acetyl]amino]methyl]-7-oxabicyclo[2.2.1]hept-2-yl]-6-octen-2-one Following the procedure of Example 1 Part F except substituting the above Part D acid for the Example 1 Part E acid, the title compound is obtained.

EXAMPLE 9

[1S-[1β,2α(5Z),3α,4β]]-1-Acetoxy-8-b [3-[[[[methyl(1-oxohexyl)amino]acetyl]amino]methyl]-7-oxabicyclo[2.2.1]hept-2-yl]-6-octen-2-one Following the procedure of Example 2 except substituting the Example 8 compound for the Example 1 compound, the title compound is obtained.

EXAMPLE 10

[1S-[1β,2α(5Z),3α,4β]]-1-Hydroxy-8-[3-[[[[methyl(1-oxohexyl)amino]acetyl]amino]-7-oxabicyclo[2.2.1]hept-2-yl]-6-octen-2-one Following the procedure of Example 3 except substituting the Example 9 compound for the Example 2 compound, the title compound is obtained.

EXAMPLE 11

[1S-[1β,2α(5Z),3α,4β]]-1-Chloro-8-[3-[[[[(Butoxycarbonyl)amino]acetyl]amino]methyl]-7-oxabicyclo[2.2.1]hept-2-yl]-6-octen-2-one

A. N-(Butoxycarbonyl)glycine ethyl ester

Glycine ethyl ester.HCl (3.5 g, 25 mmol) was suspended in distilled CH$_2$Cl$_2$ (25 ml) in an argon atmosphere. After cooling to −40° C. distilled Et$_3$N (7.65 ml, 55 mmol) was added followed by dropwise addition of a solution of distilled n-butyl chloroformate (3.2 ml, ~25 mmol) in CH$_2$Cl$_2$ (10 ml). After stirring at −40° for 1 hour the mixture was left in a freezer (−5° C.) overnight. The mixture was stirred at −5° to −10° for 1 hour. More CH$_2$Cl$_2$ was added followed by water (50 ml). The layers were separated. The organic layer was washed with 1N HCl (50 ml), saturated NaHCO$_3$ solution (50 ml) and water (50 ml), dried (MgSO$_4$), and freed of solvent in vacuo leaving 3.129 g of material. This was combined with material from a 5 mmol run and chromotographed on silica gel (100 g, Baker for flash chromatography), eluting with ether-hexane 1:1 to give the title compound as an oil (3.196 g, 52.5%). TLC: silica gel, Et$_2$O-hexane 1:1, PMA, R$_f$=0.34.

B. N-(Butoxycarbonyl)glycine

The ethyl ester prepared in part A (3.141 g, 15.47 mmol) was dissolved in 100 ml distilled THF and treated with 1N LiOH solution (40 ml). The mixture was left stirring overnight at room temperature. After acidification with concentrated HCl and addition of solid KCl, the layers were separated. The aqueous layer was reextracted with EtOAc (3×50 ml). The combined organic layers (THF+EtOAc) were washed with saturated NaCl solution (25 ml), dried (MgSO$_4$) and freed of solvent in vacuo leaving the title compound (2.78 g, quant.) which slowly crystallized.

C.

[1S-[1β,2α(5Z),3α,4β]]-7-[3-[[[[(Butoxycarbonyl)amino]acetyl]amino]methyl]-7-oxabicyclo[2.2.1]hept-2-yl]-5-heptenoic acid, methyl ester The acid prepared in part B (175.2 mg, 1 mmol) was dissolved in distilled THF (8 ml) in an argon atmosphere. After cooling in an ice bath carbonyldiimidazole (CDI) (162 mg, 1 mmol) was added. The mixture was stirred cold 1 hour and at room temperature 1 hour. The mixture was again cooled in an ice bath and a solution of chiral amine (prepared in Example I part C, 267 mg, 1 mmol) in THF (3 ml) was added. The cooling bath was removed and the mixture was left stirring overnight at room temperature. The solvent was removed in vacuo. $CHCl_3$ (35 ml) was added. The solution was washed with 1N HCl (15 ml), 1N NaOH (15 ml) and $H_2O$ (15 ml), dried ($MgSO_4$) and freed of solvent in vacuo. The remaining oil (433 mg) was chromatographed on silica gel (20 g of Baker for flash chromatography) eluting with EtOAc to give partially purified material (291 mg). This was rechromatographed on silica gel (20 g), eluting with $Et_2O$ and 2% MeOH in $Et_2O$ to give the title compound (172 mg, 40.5%) as an oil. Additional material (57 mg, 13.4%) was contaminated with a small amount of slower moving material. TLC: silica gel, 5% MeOH in $Et_2O$, vanillin, $R_f=0.32$.

D.

[1S-]1β,2α(5Z),3α,4β]]-7-[3-[[[[(Butoxycarbonyl)amino]acetyl]amino]methyl]-7-oxabicyclo[2.2.1]hept-2-yl]-5-heptenoic acid The methyl ester prepared in Part C (168 mg, 0.396 mmol) was dissolved in distilled THF (16 ml) and water (3.8 ml) in an argon atmosphere and 1N LiOH solution (3.9 ml) was added. The mixture was stirred at room temperature 5½ hours, then neutralized with 1N HCl solution (3.8 ml). After adding solid KCl the layers were separated. The aqueous layer was reextracted with $CHCl_3$ (3×25 ml). The combined organic layers (THF+$CHCl_3$) were washed with saturated NaCl solution (15 ml), dried ($MgSO_4$) and freed of solvent in vacuo leaving an oil (150 mg). This was chromatographed on silica gel (10 g, Baker for flash chromatography) eluting with 4% MeOH in $CH_2Cl_2$ to give 77 mg of material which appeared clean by TLC: silica gel, 10% MeOH in $CH_2Cl_2$, vanillin, $R_f=0.43$. The material became partially crystalline on standing several days in the cold room. Trituration with $Et_2O$ gave the title compound as a white solid (58.5 mg, 36%) m.p. 104°–106° C.

Anal Calcd for $C_{21}H_{34}O_6N_2$: C, 61.44; H, 8.35; N, 6.82; Found: C, 61.50; H, 8.37; N, 6.98.

E.

[1S-[1β,2α(5Z),3α,4β]]-1-Chloro-8-[3-[[[[(butoxycarbonyl)amino]acetyl]amino]methyl]-7-oxabicyclo[2.2.1]hept-2-yl]-6-octen-2-one Following the procedure of Example 1 Part F except substituting the above Part D acid for the Example 1 Part E acid, the title compound is obtained.

EXAMPLE 12

[1S-[1β,2α(5Z),3α,4β]]-1-Acetoxy-8-[3-]]](butoxycarbonyl)amino]acetyl]amino]methyl]-7-oxabicyclo[2.2.1]hept-2-yl]-6-octen-2-one Following the procedure of Example 2 except substituting the Example 11 compound for the Example 1 compound, the title compound is obtained.

EXAMPLE 13

[1S-[β,2α(5Z),3α,4β]]-1-Hydroxy-8-[3-[[[[(butoxycarbonyl)amino]acetyl]amino]methyl]-7-oxabicyclo[2.2.1]hept-2-yl]-6-octen-2-one Following the procedure of Example 3 except substituting the Example 12 compound for the Example 2 compound, the title compound is obtained.

EXAMPLE 14

[1S-[1β,2α(5Z),3α,4β]]-1-Chloro-3,3-difluoro-8-[3-[[[[(1-Oxohexyl)amino]acetyl]amino]methyl]-7-oxabicyclo[2.2.1]hept-2-yl]-6-octen-2-one

A.

[1S-[1β,2α,3α4β]]-2-[3-[[[[(1-Oxohexyl)amino]acetyl]amino]methyl]-7-oxabicyclo[2.2.1]hept-2-yl]-acetaldehyde $O_3$ is bubbled through a magnetically stirred solution of [1S-[1β,2α(5Z),3α,4β]]-7-[3-[[[[(1-oxohexyl)amino]acetyl]amino]methyl]-7-oxabicyclo[2.2.1]hept-2-yl]-5-heptenoic acid, methyl ester (211 mg, 0.5 mmol) (prepared as described in Example 1) in $CH_2Cl_2$/MeOH (10 ml/10 ml) at −78° C., until the solution becomes blue. Excess $O_3$ is then purged by a stream of $N_2$ and $(CH_3)_2S$ (1 ml) is added. The reaction is allowed to warm to room temperature and poured into $CH_2Cl_2$ (50 ml), $H_2O$ (10 ml). The products are extracted into $CH_2Cl_2$ layers. The $H_2O$ layer separated is re-extracted with $CH_2Cl_2$ (30 ml). The combined $CH_2Cl_2$ layers are washed with brine (10 ml) and dried over $MgSO_4$. Filtration and evaporation of solvent gives a crude product which is purified by silica gel column chromatography to afford the title compound.

B. (4-Carboxy-3,3-difluorobutyl)triphenylphosphonium bromide

(1) Methyl tetrahydrofuroate

Methyl furoate (75 g, 0.595 mole) was dissolved in MeOH (150 ml), and poured into a Parr bottle. Air was replaced with argon, and then 10% Pd/C (2.5 g) was added. The atmosphere was replaced with $H_2$ and methyl furoate was hydrogenated at 40 psi for 48 hours. The reaction was filtered through celite pad, and the pad was washed with ether. The filtrate and the wash were combined and distilled to give the title compound (71 g, 0.546 mole, 59° C./5.1 mmHg, 92%) as a colorless liquid.

(2) Methyl 2-acetoxy-5-bromopentanoate

HBr gas was bubbled into $Ac_2O$ (200 ml) at 0° C. for 2 hours. The specific gravity became 1.4. Part 1) methyl tetrahydrofuroate (70 g, 0.538 mole) was added dropwise under magnetic stirring at 0° C. and the reaction was allowed to warm to room temperature. After stirring overnight, the reaction was poured into ice (~1200 ml) carefully, and left for 30 minutes with occasional swirling. The products were extracted with $Et_2O$ (600 ml=2 and 300 ml). The combined $Et_2O$ layers were washed with dilute NaOH (~0.5%) solution, until the wash became basic. The Et$_2$O layer was further washed with H$_2$O, dried over Na$_2$SO$_4$, and filtered. The filtrate was concentrated and distilled to give the title compound (116 g, 0.458 mole, 108° C./1 mmHg, 85%) as a colorless liquid.

(3) Methyl 5-bromo-2-hydroxypentanoate

MeOH (100 ml, distilled over Mg(OMe)$_2$) was saturated with HBr gas at 0° C. This was added to Part 2) compound (60 g, 0.237 mole) in MeOH (200 ml distilled over Mg(OMe)$_2$). The reaction was allowed to warm to room temperature and stirred overnight. The reaction was concentrated in vacuo. Toluene (200 ml) was added to the resulting liquid, and the reaction was concentrated. The same process was repeated twice. The resulting liquid was dissolved in EtOAc (2000 ml) and washed with 0.5% NaOH, brine, and dried over MgSO$_4$. Filtration and evaporation of solvent gave a straw colored oil (44.8 g). This was distilled to give the title compound (34 g, 0.161 mole, 68%) as a colorless liquid.

(4) Methyl 5-bromo-2-oxopentanoate

Jones' reagent (CrO$_3$: 9.58 g, H$_2$SO$_4$: 8.47 ml, H$_2$O: 36.8 ml) was added to a magnetically stirred solution of Part 3) compound (12.53 g, 59.3 mmole) in acetone (150 ml) at room temperature. The addition was controlled to maintain the temperature below 35° C. After the completion of the addition, the reaction was stirred at room temperature for 45 minutes. Isopropyl alcohol (30 ml) was added dropwise and stirred for 30 minutes. The reaction was then diluted with H$_2$O (500 ml) and the products were extracted with CH$_2$Cl$_2$ (1 l.) The CH$_2$Cl$_2$ layer was washed with brine (100 ml×3) and dried over MgSO$_4$. Filtration and evaporation of solvents gave the title compound (11.4 g, 54.5 mmole, 92%) as a colorless liquid.

(5) Methyl 5-bromo-2,2-difluoropentanoate

Part (4) compound (11.4 g, 54.5 mmole) was added dropwise to (C$_2$H$_5$)$_2$NSF$_3$ (DAST) (6.8 ml, 55.7 mmole) at room temperature. The container of Part (4) was rinsed with CH$_2$Cl$_2$ (20 ml), which was added to the reaction. The reaction was stirred at room temperature for 1 hour and poured into H$_2$O (80 ml). The products were extracted with CH$_2$Cl$_2$ (40 ml×3). The combined CH$_2$Cl$_2$ layers were washed with H$_2$O (20 ml×3) and dried over MgSO$_4$. Filtration and evaporation of solvent gave a straw colored liquid (10.8 g). This was distilled to give the title compound (8.4 g, 36.3 mmole, 67%, 41° C./0.015 mmHg) as a colorless liquid.

(6) 5-Bromo-2,2-difluoropentanoic acid

HBr gas was introduced into 48% HBr in H$_2$O (100 ml) with occasional cooling in an ice bath until the weight became 180 g. The HBr solution was then added to Part (5) compound (8.4 g, 36.3 mmole) at room temperature and the reaction was stirred for 5 hours at room temperature. The reaction was cooled to 0° C. and poured into Et$_2$O (900 ml) in an ice bath. The products were extracted into the Et$_2$O layer. The water layer was further extracted with Et$_2$O (200 ml and 100 ml). The combined ether layers were washed with H$_2$O (200 ml). The H$_2$O wash was backwashed with Et$_2$O (100 ml). The Et$_2$O layers were combined and dried over MgSO$_4$. Filtration and evaporation of solvent gave the title compound (7.8 g, quant.) as a colorless liquid.

(7) (4-Carboxy-3,3-difluorobutyl)triphenylphosphonium bromide

Acetonitrile (23 ml) was added to a mixture of triphenylphosphine (6.7 g, 25.7 mmole) and Part (6) compound (4.6 g, 21.2 mmole). The solution was heated at gentle reflux under magnetic stirring for 30 hours. Toluene (46 ml) was then added and the reaction was brought to reflux for a brief period. The reaction was allowed to cool to 5° C. and kept overnight. The resulting white precipitates were collected, washed with cold acetonitrile/toluene (1/2), and dried in a heated vacuum oven (60°C. ~5 mmHg) to give the title bromide (9.8 g, 20.4 mmole, 96.5%) as white solid.

C. [1S-[1β,2α(5Z),3α,4β]]-2,2-Difluoro-7-[3-[[[[(1-oxohexyl)amino]acetyl]amino]methyl]-7-oxabicyclo[2.2.1]hept-2-yl]-5-heptenoic acid (4-Carboxy-3,3-difluorobutyl)triphenylphosphonium bromide (1.27 g) (prepared in Part B) is suspended in THF (15 ml). KOt-Amylate (1.7M in toluene, 3 ml) is added at room temperature. The reaction is stirred for 4 hours. The resulting solution is transferred dropwise to aldehyde obtained in Part A, (177.1 mg) in THF (10 ml) at 0° C. The reaction is warmed to room temperature and stirred for 15 hours. Saturated NH$_4$Cl (25 ml) is added and the products are extracted with EtOAc (40 ml×3). The combined organic layers are washed with brine (30 ml) and dried over MgSO$_4$. Filtration and evaporation of solvents afford a brown colored oil, which is purified by silica gel column to give the title compound.

D. [1S-[1β,2α(5Z),3α,4β]]-1-Chloro-3,3-difluoro-8-[3-[[[[(1-oxohexyl)amino]acetyl]amino]methyl]-7-oxabicyclo[2.2.1]hept-2-yl]-6-octen-2-one Following the procedure of Example 1 Part F except substituting the above Part C acid for the Example 1 Part E acid, the title compound is obtained.

EXAMPLE 15

[1S-[1β,2α(5Z),3α,4β]]-1-Acetoxy-3,3-difluoro-8-[3-[[[[(1-oxohexyl)amino]acetyl]amino]methyl]-7-oxabicyclo[2.2.1]hept-2-yl]-6-octen-2-one Following the procedure of Example 2 except substituting the Example 14 compound for the Example 1 compound, the title compound is obtained.

EXAMPLE 16

[1S-[1β,2α(5Z),3α,4β]]-1-Hydroxy-3,3-difluoro-8-[3-[[[[(1-oxohexyl)amino]acetyl]amino]methyl]-7-oxabicyclo[2.2.1]hept-2-yl]-6-octen-2-one Following the procedure of Example 3 except substituting the Example 15 compound for the Example 2 compound, the title compound is obtained.

EXAMPLE 17

[1S-[1β,2α(2E,5Z),3α,4β]]-1-Chloro-8-[3-[[[[(1-Oxohexyl)amino]acetyl]amino]methyl]-7-oxabicyclo[2.2.1]hept-2-yl]-3,6-octadien-2-one

A.
[1S-[1β,2α(5Z),3α,4β]]-7-[3-[[[[(1-Oxohexyl)amino]acetyl]amino]methyl]-7-oxabicyclo[2.2.1]hept-2-yl]-2,5-heptadienoic acid (4-Carboxy-2-butenyl)triphenylphosphonium bromide (1.13 g) is suspended in THF (15 ml). KOt Amylate (1.7M in toluene, 3 ml) is added at room temperature. The reaction is stirred for 4 hours. The resulting solution is transferred dropwise to aldehyde obtained in Example 9 Part A, (177.1 mg) in THF (10 ml) at 0° C. The reaction is warmed to room temperature and stirred for 15 hours. Saturated NH₄Cl (25 ml) is added and the products are extracted with EtOAc (40 ml×3). The combined organic layers are washed with brine (30 ml) and dried over MgSO₄. Filtration and evaporation of solvents afford a crude product, which is purified by silica gel column to give the title compound.

B.
[1S-[1β,2α(5Z),3α,4β]]-1-Chloro-8-[3-[[[[(1-oxohexyl)amino]acetyl]amino]methyl]-7-oxabicyclo[2.2.1]hept-2-yl]-3,6-octadien-2-one Following the procedure of Example 1 Part F except substituting the above Part A acid for the Example 1 Part E acid, the title compound is obtained.

EXAMPLE 18

[1S-[1β,2α(5Z),3α,4β]]-1-Acetoxy-8-[3-[[[[(1-oxohexyl)amino]acetyl]amino]methyl]-7-oxabicyclo[2.2.1]hept-2-yl]-3,6-octadien-2-one Following the procedure of Example 2 except substituting the Example 17 compound for the Example 1 compound, the title compound is obtained.

EXAMPLE 19

[1S-[1β,2α(5Z),3α,4β]]-1-Hydroxy-8-[3-[[[[(1-oxohexyl)amino]acetyl]amino]methyl]-7-oxabicyclo[2.2.1]hept-2-yl]-3,6-octadien-2-one Following the procedure of Example 3 except substituting the Example 18 compound for the Example 2 compound, the title compound is obtained.

EXAMPLE 20

[1S-[1β,2α(5Z),3α(R),4β]]-1-Chloro-8-[3-[[[1-oxo-2-[(-Oxohexyl)amino]propyl]amino]methyl]-7-oxabicyclo[2.2.1]hept-2-yl]-6-octen-2-one

A. (2R)-2-(Hexanoylamino)propionic acid

D-alanine (20 mmol) and hexanoyl chloride (22 mmol) were reacted using the method as described in Example 5 Part A to give the title compound as a white crystalline material (2.45 g, 65.5%) after recrystallization from isopropyl ether (20 ml), m.p. 82°-95° C.

B.
[1S-[1β,2α(5Z),3α(R),4β]]-7-[3-[[[1-Oxo-2-[(1-Oxohexyl)amino]propyl]amino]-methyl]-7-oxabicyclo[2.2.1]hept-2-yl]-5-heptenoic acid, methyl ester Part A acid compound (1 mmol) and chiral amine prepared as described in Example 1 Part C (1 mmol) were coupled using CDI (1 mmol) as described in Example 5 Part B. The crude product was chromatographed on silica gel (Baker for flash chromatography) eluting with 2–4% MeOH in Et₂O. The eluted product was triturated with Et₂O to give the title methyl ester as a white solid (217 mg, 50%).

TLC: silica gel, 5% MeOH in Et₂O, vanillin $R_f$=0.47.

C.
[1S-[1β,2α(5Z),3α(R),4β]]-7-[3-[[[1-Oxo-2-[(1-Oxohexyl)amino]propyl]amino]methyl]-7-oxabicyclo[2.2.1]hept-2-yl]-5-heptenoic acid The part B methyl ester (215 mg, 0.49 mmol) was hydrolyzed with LiOH solution in a THF-water mixture as described in Example 6. The viscous product was dissolved in EtOAc (~2-3 ml). On standing crystalline material was deposited. This was harvested by filtration and washed with Et₂O to give title acid (166.6 mg, 80%), m.p. 101°-103°.

Anal Calcd for $C_{23}H_{38}O_5N_2$: C, 65.37; H, 9.06; N, 6.63; Found: C, 65.30; H. 9.16; N, 6.46.

TLC: Silica gel, 10% MeOH in $CH_2Cl_2$, vanillin, $R_f$=0.48.

$[\alpha]_D$= +25.5° (c=1.37, MeOH).

D.
[1S-[1β,2α(5Z),3α,4β]]-1-Chloro-8-[3-[[[1-oxo-2-[(1-oxohexyl)amino]propyl]amino]methyl]-7-oxabicyclo[2.2.1]hept-2-yl]-6-octen-2-one Following the procedure of Example 1 Part F except substituting the above Part C acid for the Example 1 Part E acid, the title compound is obtained.

EXAMPLE 21

[1S-[1β,2α(5Z),3α,4β]]-1-Acetoxy-8-[3-[[[1-oxo-2-[(1-oxohexyl)amino)propyl]amino]methyl]-7-oxabicyclo[2.2.1]hept-2-yl]-6-octen-2-one Following the procedure of Example 2 except substituting the Example 20 compound for the Example 1 compound, the title compound is obtained.

EXAMPLE 22

[1S-[1β,2α(5Z),3α,4β]]-1-Hydroxy-8-[3-[[[1-oxo-2-[(1-oxohexyl)amino]propyl]amino]methyl]-7-oxabicyclo[2.2.1]hept-2-yl]-6-octen-2-one Following the procedure of Example 3 except substituting the Example 21 compound for the Example 2 compound, the title compound is obtained.

EXAMPLE 23

[1S-[1β,2α(5Z),3α(S),4β]]-1-Chloro-8-[3-[[[1-Oxo-2-[(1-oxohexyl)amino]propyl]amino]methyl]-7-oxabicyclo[2.2.1]hept-2-yl]-6-octen-2-one

A. (2S)-2-(Hexanoylamino)propionic acid

L-Alanine (10 mmol) and hexanoyl chloride (11 mmol) were reacted using the method described in Example 5 Part A to give the title compound as a white crystalline material (1.091 g, 58%) after recrystallization from isopropyl ether (~6 ml).

B.
[1S-[1β,2α(5Z),3α(S),4β]]-7-[3-[[[1-Oxo-2-[(1-oxohexyl)amino]propyl]amino]methyl]-7-oxabicyclo[2.2.1]hept-2-yl]-5-heptenoic acid, methyl ester Part A compound (1 mmol) and chiral amine (prepared as described in Example 1 Part C) (1 mmol) were coupled using CDI (1 mmol) as described in Example 5

Part B. The crude product was chromatographed on silica gel (Baker for flash chromatography) eluting with 2% MeOH in Et$_2$O to give clean title methyl ester (178 mg, 41%) and additional material (129 mg, 29%) contaminated with material moving slower on TLC. TLC: silica gel, 5% MeOH in Et$_2$O, vanillin, R$_f$=0.55. Slower moving contaminant R$_f$=0.34.

C.

[1S-[1β,2α(5Z),3α(S),4β]]-7-[3-[[[1-Oxo-2-[(1-oxohexyl)amino]propyl]amino]methyl]-7-oxabicyclo[2.2.1-]hept-2-yl]-5heptenoic acid The Part B methyl ester (175 mg, 0.40 mmol) was hydrolyzed with LiOH in a THF-water mixture as described in Example 1. The viscous product was dissolved in EtOAc (2 ml). Crystalline material was deposited on standing. This was harvested by filtration and washed with cold Et$_2$O to give the title compound (129 mg, 76%), m.p. 104°–106° C.

Anal Calcd for C$_{23}$H$_{38}$O$_5$N$_2$: C, 65.37; H, 9.06; N, 6.63; Found: C, 65.53; H, 9.26; N, 6.50.

TLC: silica gel, 10% MeOH in CH$_2$Cl$_2$, vanillin, R$_f$=0.48.

[α]$_D$= −40° (C=1.29, MeOH)

D.

[1S-[1β,2α(5Z),3α,4β]]-1-Chloro-8-[3-[[[1-oxo-2-[(1-oxohexyl)amino]propyl]amino]methyl]-7-oxabicyclo[2.2.1]hept-2-yl]-6-octene-2-one Following the procedure of Example 1 Part F except substituting the above Part C acid for the Example 1 Part E acid, the title compound is obtained.

EXAMPLE 24

[1S-[1β,2α(5Z),3α,4β]]-1-Acetoxy-8-[3-[[[1-oxo-2-[(1-oxohexyl)amino]propyl]amino]methyl]-7-oxabicyclo[2.2.1]hept-2-yl]-6-octen-2-one Following the procedure of Example 2 except substituting the Example 23 compound for the Example 1 compound, the title compound is obtained.

EXAMPLE 25

[1S-[1β,2α(5Z),3α,4β]]-1-Hydroxy-8-[3-[[[1-oxo-2-[(1-oxohexyl)amino]propyl]amino]methyl]-7-oxabicyclo[2.2.1]hept-2-yl]-6-octene-2-one Following the procedure of Example 3 except substituting the Example 24 compound for the Example 2 compound, the title compound is obtained.

EXAMPLE 26

[1S-[1β,2α(5Z),3α,4β]]-1-Chloro-8-[3-[[[2-methyl-2-[(1-Oxohexyl)amino]-1-oxopropyl]amino]methyl]-7-oxabicyclo[2.2.1]hept-2-yl]-6-octen-2-one

A. 2-Hexanoylamino)-2-methylpropionic acid

2-Aminoisobutyric acid (2.0 g, 19.4 mmol) and n-hexanoyl chloride (3.0 g, 22.4 mmol) were reacted in the presence of NaOH (1.6 g, 40 mmol) in a mixture of ether and water using the method described in Example 5, Part A. The title compound (1.90 g, 49%) was obtained after crystallization from benzene, m.p. 141°–143° C.

B.

[1S-[1β,2α(5Z),3α,4β]]-7-[3-[[[2-Methyl-2-[(1-Oxohexyl)amino]-1-oxopropyl]amino]methyl]-7-oxabicyclo[2.2.1]hept-2-yl]-5-heptenoic acid, methyl ester Part A compound (1 mmol) was reacted with CDI (1 mmol) and then with chiral amine prepared as described in Example 1 Part C (1 mmol) employing the method described in Example 1 Part D. The crude product was chromatographed on silica gel (25 g, Baker for flash chromatography), eluting with 2% MeOH in Et$_2$O to give title ester (235 mg, 52%) as white crystalline material.

TLC: silica gel, 5% MeOH in Et$_2$O, vanillin, R$_f$=0.46.

C.

[1S-[1β,2α(5Z),3α,4β]]-7-[3-[[[2-Methyl-2-[(1-oxohexyl)amino]-1-oxopropyl]amino]methyl]-7-oxabicyclo[2.2.1]hept-2-yl]-5-heptenoic acid The Part B methyl ester (231 mg, 0.51 mmol) was hydrolyzed with LiOH in a water-THF mixture as described in Example 6. The product was crystallized from ethyl acetate (~4 ml) to give title acid (154.2 mg, 69%), m.p. 81°–87° C.

TLC: silica gel, 10% MeOH in CH$_2$Cl$_2$, vanillin, R$_f$=0.42.

[α]$_D$= −10.1° (c=1.63, MeOH)

Anal Calcd for C$_{24}$H$_{40}$O$_5$N$_2$: C, 66.02; H, 9.24; N, 6.42; Found: C, 65.92; H, 9.37; N, 6.46.

D.

[1S-[1β,2α(5Z),3α,4β]]-1-Chloro-8-[3-[[[2-methyl-2-[(1-oxohexyl)amino]-1-oxopropyl]amino]methyl]-7-oxabicyclo[2.2.1]hept-2-yl]-6-octen-2-one Following the procedure of Example 1 Part F except substituting the above Part C acid for the Example 1 Part E acid, the title compound is obtained.

EXAMPLE 27

[1S-[1β,2α(5Z),3α,4β]]-1-Acetoxy-8-[3-[[[2-methyl-2-[(1-oxohexyl)amino]-1-oxopropyl]amino]methyl]-7-oxabicyclo[2.2.1]hept-2-yl]-6-octen-2-one Following the procedure of Example 2 except substituting the Example 26 compound for the Example 1 compound, the title compound is obtained.

EXAMPLE 28

[1S-[1β,2α(5Z),3α,4β]]-1-Hydroxy-8-[3-[[[2-methyl-2-[(1-oxohexyl)amino]-1-oxopropyl]amino]methyl]-7-oxabicyclo[2.2.1]hept-2-yl]-6-octen-2-one Following the procedure of Example 3 except substituting the Example 27 compound for the Example 2 compound, the title compound is obtained.

EXAMPLE 29

[1S-[1β,2α(5Z),3α,4α]]-1-Chloro-8-[3-[[[[(1-Oxoheptyl)amino]acetyl]amino]methyl]-7-oxabicyclo[2.2.1]hept-2-yl]-6-octen-2-one

A. 2-(Heptanoylamino)acetic acid

Glycine (1.5 g, 20 mmol) and heptanoyl chloride (22 mmol) were reacted in the presence of NaOH (40 mmol) in a mixture of water and ether using the method described in Example 5. The crude product was recrystallized from EtOAc (30 ml) to give title compound (2.71 g, 72%), m.p. 98°–100° C.

B.
[1S-[1β,2α(5Z),3α,4α]]-7-[3-[[[[(1-Oxoheptyl-)amino]acetyl]amino]methyl]-7-oxabicyclo[2.2.1]hept-2-yl]-5-heptenoic acid, methyl ester Part A compound (1 mmol) was reacted with CDI (1 mmol) and then with chiral amine (1 mmole) prepared as described in Example 1 Part C employing the method described in Example 5 Part B. The crude product was chromatographed on silica gel (25 g, Baker for flash chromatography) eluting with EtOAc and 2% MeOH in EtOAc to give title ester (270 mg, 62%) as an oil. TLC: silica gel, 5% MeOH in EtOAc, vanillin, $R_f=0.45$.

C.
[1S-[1β,2α(5Z),3α,4β]]-7-[3-[[[[(1-Oxoheptyl-)amino]acetyl]amino]methyl]-7-oxabicyclo[2.2.1]hept-2-yl]-5-heptenoic acid The Part B methyl ester (265 mg, 0.607 mmol) was hydrolyzed with LiOH in a water-THF mixture as described in Example 6. The crude crystalline product was recrystallized from EtOAc (4 ml) to give title acid (204 mg, 80%), m.p. 114°–116° C.
TLC: Silica gel, 10% MeOH in $CH_2Cl_2$, vanillin, $R_f=0.40$
$[\alpha]_D = -6.6°$ (C=1.15, MeOH).
Anal Calcd for $C_{23}H_{38}O_5N_2$: C, 65.37; H, 9.06; N, 6.42; Found: C, 65.38; H, 9.01; N, 6.64.

D.
[1S-[1β,2α(5Z),3α,4β]]-1-Chloro-8-[3-[[[(1-oxoheptyl-)amino]acetyl]amino]methyl]-7-oxabicyclo[2.2.1]hept-2-yl]-6-octen-2one Following the procedure of Example 1 Part F except substituting the above Part C acid for the Example 1 Part E acid, the title compound is obtained.

EXAMPLE 30

[1S-[1β,2α(5Z),3α,4β]]-1-Acetoxy-8-[3-[[[[(1-oxoheptyl)amino]acetyl]amino]ethyl]-7-oxabicyclo[2.2.1]hept-2-yl]-6-octen-2-one Following the procedure of Example 2 except substituting the Example 29 compound for the Example 1 compound, the title compound is obtained.

EXAMPLE 31

[1S-[1β,2α(5Z),3α,4β]]-1-Hydroxy-8-[3-[[[[(1-oxohexyl)amino]acetyl]amino]methyl]-7-oxabicyclo[2.2.1-]hept-2-yl]-6-octen-2-one Following the procedure of Example 3 except substituting the Example 30 compound for the Example 2 compound, the title compound is obtained.

EXAMPLE 32

[1S-(1β,2α,3α,4β)]-1-Chloro-8-[3-[[[[(1-Oxohexyl-)amino]acetyl]amino]methyl]-7-oxabicyclo[2.2.1]hept-2-yl]-2-octanone A.
[1S-(1β,2α,3α,4β)]-7-[3-(Hydroxymethyl)-7-oxabicyclo[2.2.1]hept-2-yl]heptanoic acid, methyl ester To 800 mg (3.0 mmole) of the [1S-[1β,2α(Z),3α,4β]]-7-[3-(hydroxymethyl)-7-oxabicyclo[2.2.1]hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.
[1S-(1β,2α,3α,4β)]-7-[3-[[[[(1-Oxohexyl)amino]acetyl]amino]methyl]-7-oxabicyclo[2.2.1hept-2-yl]heptanoic acid, methyl ester Following the procedure of Example 1 except substituting the Part A alcohol-ester for the alcohol ester employing in Example 1 Part B, the title compound is obtained.

C.
[1S-(1β,2α,3α,4β)]-1-Chloro-8-[3-[[[[(1-oxohexyl-)amino]acetyl]amino]methyl]-7-oxabicyclo[2.2.1]hept-2-yl]-6-octanone Following the procedure of Example 1 Parts E and F except substituting the above Part B ester for the Example 1 Part D ester, the title compound is obtained.

EXAMPLE 33

[1S-(1β,2α,3α,4β)]-1-Acetoxy-8-[3-[[[[(1-oxohexyl-)amino]acetyl]amino]methyl]-7-oxabicyclo[2.2.1]hept-2-yl]-2-octanone Following the procedure of Example 2 except substituting the Example 32 compound for the Example 1 compound, the title compound is obtained.

EXAMPLE 34

[1S-(1β,2α,3α,4β)]-1-Hydroxy-8-[3-[[[[(1-oxohexyl-)amino]acetyl]amino]methyl]-7-oxabicyclo[2.2.1]hept-2-yl]-2-octanone Following the procedure of Example 3 except substituting the Example 33 compound for the Example 2 compound, the title compound is obtained.

EXAMPLE 35

[1S-[1β,2α(5Z),3α,4β]]-1-Chloro-8-[3-[[[(1-oxo-3-[(1-oxopentyl)amino]propyl]amino]methyl]-7-oxabicyclo[2.2.1]hept-2-yl]-6-octen-2-one A. 3-Pentanoylamino)propionic acid β-Alanine (20 mmol) was reacted with valeryl chloride (22 mmol) in the presence of NaOH (40 mmol) in a mixture of $H_2O$ and ether using the method described in Example 5. The crude crystalline product (2.75 g, 79%) was recrystallized from a mixture of isopropyl ether (150 ml) and ethyl acetate (10 ml) to give title acid (1.51 g, 44%), m.p. 73°–76° C.

B.
[1S-[1β,2α(5Z),3α,4β]]-7-[3-[[[(1-Oxo-3-[(1-oxopentyl-)amino]propyl]amino]methyl]-7-oxabicyclo[2.2.1]hept-2-yl]-5-heptenoic acid, methyl ester Part A acid (1 mmol) was reacted with carbonyl diimidazole (1 mmol) followed by [1S-[1β,2α(5Z)-,3α,4β]]-7-[3-(aminomethyl)-7-oxabicyclo[2.2.1]hept-2-yl]-5-heptenoic acid, methyl ester (prepared as described in Example 1 Part C (1 mmole)). The crude product was chromatographed on silica gel (25 g, Baker for flash chromatography) eluting with 5–10% MeOH in $Et_2O$ to give title product as a white solid (304 mg, 72%).
TLC: silica gel, 10% MeOH in $Et_2O$, vanillin, $R_f=0.47$.

C.
[1S-1β,2α(5Z),3α,4β]]-7-[3-[[[1-Oxo-3-[(1-oxopentyl)amino]propyl]amino]methyl]-7-oxabicyclo[2.2.1]hept-2-yl]-5-heptenoic acid The Part B methyl ester (301 mg, 0.71 mmol) was hydrolyzed with LiOH in a THF-H$_2$O mixture as described in Example 6 to give a white solid (249 mg). This was recrystallized from EtOAc (~4 ml) to give title acid (218 mg, 75%), m.p. 113°-115°.

TLC: silica gel, 10% MeOH in CH$_2$Cl$_2$, vanillin, R$_f$=0.28

Anal Calcd for C$_{22}$H$_{36}$O$_5$N$_2$: C, 64.68; H, 8.88; N, 6.86; Found: C, 64.65; H, 8.85; N, 6.87.

$[\alpha]_D = -8.4°$ (c=1.0, MeOH)

D.
[1S-[1β,2α(5Z),3α,4β]]-1-Chloro-8-[3-[[[1-oxo-3-[(1-oxopentyl)amino]propyl]amino]methyl]-7-oxabicyclo[2.2.1]hept-2-yl]-6-octen-2-one Following the procedure of Example 1 Part F except substituting the above Part C acid for the Example 1 Part E acid, the title compound is obtained.

EXAMPLE 36
[1S-[1β,2α(5Z),3α,4β]]-1-Acetoxy-8-[3-[[[(1-oxo-3-[(1-oxopentyl)amino]propyl]amino]methyl]-7-oxabicyclo[2.2.1]hept-2-yl]-6-octen-2-one Following the procedure of Example 2 except substituting the Example 35 compound for the Example 1 compound, the title compound is obtained.

EXAMPLE 37
[1S-[1β,2α(5Z),3α,4β]]-1-Hydroxy-8-[3-[[[(1-oxopentyl)amino]acetyl]amino]methyl]-7-oxabicyclo[2.2.1]hept-2-yl]-6-octen-2-one Following the procedure of Example 3 except substituting the Example 36 compound for the Example 2 compound, the title compound is obtained.

EXAMPLE 38
[1S-[1β,2α(5Z),3α,4β]]-1-Chloro-8-[3-[[[[(4-Phenylbenzoyl)amino]acetyl]amino]methyl]-7-oxabicyclo[2.2.1]hept-2-yl]-5-heptenoic acid, methyl ester

A. 2-[(4-Phenylbenzoyl)amino]acetic acid

Glycine (5 mmol) was reacted with 4-biphenylcarbonyl chloride (about 5 mmol) in the presence of 1N NaOH solution (10 ml), ether (21 ml) and THF (2 ml) using the procedure described in Example 5. Most of the product precipitated as a solid on acidification of the aqueous layer during the work up. This was found to be quite insoluble in CHCl$_3$ and EtOAc. It was largely dissolved in CH$_3$CN (~35 ml) and filtered to remove insoluble material. Crystalline acid (0.81 g, 63%) was deposited on cooling, m.p. 207°-218° C. decomp.

B.
[1S-[1β,2α(5Z),3α,4β]]-7-[3-[[[[(4-Phenylbenzoyl)amino]acetyl]amino]methyl]-7-oxabicyclo[2.2.1]hept-2-yl]-5-heptenoic acid, methyl ester Part A acid (1 mmol) was reacted with carbonyldiimidazole (1 mmol) followed by [1S-[1β,2α(5Z),3α,4β]]-7-[3-(aminomethyl)-7-oxabicyclo[2.2.1]hept-2-yl]-5-heptenoic acid, methyl ester (1 mmole) as in Example 1, Part C. After stirring overnight at room temperature, a large amount of solid was still out of solution and TLC indicated the reaction was not complete. DMF (3 ml) was added to give a nearly clear reaction mixture and the mixture was left stirring an additional 24 hours. After the usual work up, the viscous product was chromatographed on silica gel (30 g of Baker for flash chromatography), eluting with 2% MeOH in CH$_2$Cl$_2$. The material obtained from the column was crystallized from ethyl acetate (2 ml) to give title ester (143 mg, 28%) as a white solid.

TLC: silica gel, 10% MeOH in CH$_2$Cl$_2$, UV+vanillin, R$_f$=0.51.

C.
[1S-[1β,2α(5Z),3α,4β]]-7-[[[[(4-Phenylbenzoyl)amino]acetyl]amino]methyl]-7-oxabicyclo[2.2.1]hept-2-yl]-5-heptenoic acid The Part B methyl ester (141 mg, 0.279 mmol) was hydrolyzed with LiOH as described in Example 6 to give a white solid. This was triturated with EtOAc to give title acid (118 mg, 86%), m.p. 227°-229° dec.

Anal Calcd for C$_{29}$H$_{34}$O$_5$N$_2$: C, 71.00; H, 6.99; N, 5.71; Found: C, 70.90; H, 6.91; N, 5.65.

D.
[1S-[1β,2α(5Z),3α,4β]]-1-Chloro-8-[3-[[[[(4-phenylbenzoyl)amino]acetyl]amino]methyl]-7-oxabicyclo[2.2.1]hept-2-yl]-6-octen-2-one Following the procedure of Example 1 Part F except substituting the above Part C acid for the Example 1 Part E acid, the title compound is obtained.

EXAMPLE 39
[1S-[1β,2α(5Z),3α,4β]]-1-Acetoxy-8-[3-[[[[(4-phenylbenzoyl)amino]acetyl]amino]methyl]-7-oxabicyclo[2.2.1]hept-2-yl]-6-octen-2-one Following the procedure of Example 2 except substituting the Example 38 compound for the Example 1 compound, the title compound is obtained.

EXAMPLE 40
[1S-[1β,2α(5Z),3α,4β]]-1-Hydroxy-8-[3-[[[[(4-phenylbenzoyl)amino]acetyl]amino]methyl]-7-oxabicyclo[2.2.1]hept-2-yl]-6-octen-2-one Following the procedure of Example 3 except substituting the Example 39 compound for the Example 2 compound, the title compound is obtained.

EXAMPLE 41
[1S-(1β,2α,3α,4β)]-1-Hydroxy-8-[3-[[[[2-Methyl-2-[(1-oxohexyl)amino]-1-oxopropyl]amino]methyl]-7-oxabicyclo[2.2.1]hept-2-yl]-2-octanone Following the procedure of Example 32 except substituting the Example 26 Part A acid for the Example 1 Part A acid, the title acid is obtained.

EXAMPLE 42
[1S-[1β,2α(5Z),3α,4β]]-1-Hydroxy-8-[3-[[[[(1-Oxopropyl)amino]acetyl]amino]methyl]-7-oxabicyclo[2.2.1]hept-2-yl]-6-octen-2-one Following the procedure of Examples 1 to 3 except substituting propanoyl chloride for hexanoyl chloride, the title compound is obtained.

EXAMPLE 43

[1S-[1β,2α(5Z),3α,4β]]-1-Hydroxy-8-[[[[(1-Oxoethyl)amino]acetyl]amino]methyl]-7-oxabicyclo[2.2.1]hept-2-yl]-6-octen-2-one Following the procedure of Examples 1 to 3 except substituting acetyl chloride for 6-hexanoyl chloride, the title compound is obtained.

EXAMPLE 44

[1S-[1β,2α(5Z),3α,4β]]-1-Hydroxy-8-[3-[[[[(1-Oxo-2-butenyl)amino]acetyl]amino]methyl]-7-oxabicyclo[2.2.1]hept-2-yl]-6-octen-2-one Following the procedure of Examples 1 to 3 except substituting 2-butenoyl chloride for hexanoyl chloride, the title compound is obtained.

EXAMPLE 45

[1S-[1β,2α(5Z),3α,4β]]-1-Hydroxy-8-[3-[[[[(1-Oxo-3-butynyl)amino]acetyl]amino]methyl]-7-oxabicyclo[2.2.1]hept-2-yl]-6-octen-2-one Following the procedure of Examples 1 to 3 except substituting 3-butynoyl chloride for hexanoyl chloride, the title compound is obtained.

EXAMPLE 46

[1S-[1β,2α(5Z),3α,4β]]-1-Hydroxy-8-[3-[[[[[(Pentylamino)carbonyl]amino]acetyl]amino]methyl]-7-oxabicyclo[2.2.1]hept-2-yl]-6-octen-2-one Following the procedure of Examples 4 to 6 except substituting n-pentyl isocyanate for n-butyl isocyanate, the title compound is obtained.

EXAMPLE 47

[1S-[1β,2α(5Z),3α,4β]]-1-Hydroxy-8-[3-[[[[[(Phenylamino)carbonyl]amino]acetyl]amino]methyl]-7-oxabicyclo[2.2.1]hept-2-yl]-6-octen-2-one Following the procedure of Examples 4 to 6 except substituting phenyl isocyanate for n-butyl isocyanate, the title compound is obtained.

EXAMPLE 48

[1S-[1β,2α(5Z),3α,4β]]-1-Hydroxy-8-[3-[[[[(Phenylcarbonyl)amino]acetyl]amino]methyl]-7-oxabicyclo[2.2.1]hept-2-yl]-6-octen-2-one Following the procedure of Examples 1 to 3 except substituting benzoyl chloride for hexanoyl chloride, the title compound is obtained.

EXAMPLE 49

[1S-[1β,2α(5Z),3α,4β]]-1-Hydroxy-8-[3-[[[1-Oxo-3-[ethyl(phenylcarbonyl)amino]propyl]amino]methyl]-7-oxabicyclo[2.2.1]hept-2-yl]-6-octen-2-one Following the procedure of Examples 7 to 9 except substituting 3-(ethylamino)propionic acid for sarcosine and benzoyl chloride for hexanoyl chloride, the title compound is obtained.

EXAMPLE 50

[1S-[1β,2α(5Z),3α,4β]]-1-Hydroxy-8-3-[[[[(Benzyloxycarbonyl)amino]acetyl]amino]methyl]-7-oxabicyclo[2.2.1]hept-2-yl]-6-octen-2-one Following the procedure of Examples 1 to 12 except substituting benzyl chloroformate for n-butyl chloroformate, the title compound is obtained.

EXAMPLE 51

[1S-(1β,2α,3α,4β)]-1-Hydroxy-8-[3-[[[[(1-Oxobutyl)amino]acetyl]amino]methyl]-7-oxabicyclo[2.2.1]-hept-2-yl]-2-octanone Following the procedure of Examples 32 to 34 except substituting butanoyl chloride for hexanoyl chloride, the title compound is obtained.

EXAMPLE 52

[1S-(1β,2α,3α,4β)]-1-Hydroxy-8-[3-[[[[(1-Oxo-2-propenyl)amino]acetyl]amino]methyl]-7-oxabicyclo[2.2.1]hept-2-yl]-2-octanone Following the procedure of Examples 32 to 34 except substituting propenyl chloride for hexanoyl chloride, the title compound is obtained.

EXAMPLE 53

[1S-(1β,2α,3α,4β)]-1-Hydroxy-8-[3-[[[[(1-Oxo-4-pentynoyl)amino]acetyl]amino]methyl]-7-oxabicyclo[2.2.1-]hept-2-yl]-2-octanone Following the procedure of Examples 32 to 34 except substituting 4-pentynoyl chloride for hexanoyl chloride, the title compound is obtained.

EXAMPLE 54

[1S-(1β,2α,3α,4β)]-1-Hydroxy-8-[3-[[[[[(Phenylamino)carbonyl]amino]acetyl]amino]methyl]-7-oxabicyclo[2.2.1]hept-2-yl]-2-octanone Following the procedure of Examples 32 to 34 except substituting phenyl isocyanate for n-butyl isocyanate in Example 3 Part A, the title compound is obtained.

EXAMPLE 55

[1S-(1β,2α,3α,4β)]-1-Hydroxy-8-[3-[[[1-Oxo-4-[propyl(benzoyl)amino]butyl]amino]methyl]-7-oxabicyclo[2.2.1]hept-2-yl]-2-octanone Following the procedure of Examples 32 to 34 and 7 to 9 except substituting 4-(propylamino)butanoic acid for sarcosine in Example 7 Part A, the title compound is obtained.

EXAMPLE 56

[1S-(1β,2α,3α,4β)]-1-Hydroxy-8-[3-[[[[(Benzyloxycarbonyl)amino]acetyl]amino]methyl]-7-oxabicyclo[2.2.1-]hept-2-yl]-2-octanone Following the procedure of Examples 32 to 34 and 10 to 12 except substituting benzyl chloroformate for n-butyl chloroformate, the title compound is obtained.

EXAMPLE 57

[1S-[1β,2α(5Z),3α,4β]]-1-Chloro-8-[3-[2-[[[(1-Oxohexyl)amino]acetyl]amino]ethyl]-7-oxabicyclo[2.2.1]hept-2-yl]-6-octen-2-one

A.
[1S-[1β,2α(Z),3α,4β]]-7-[3-(2-Oxo)ethyl-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride (($C_6H_5$)$_3$P+—$CH_2OCH_3Cl^-$) and 235 ml distilled toluene (stored over molecular sieves). The resulting suspension was stirred in an ice-bath, under argon, until cold and than a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1S-[1β,2α(5Z),3α,4β]]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml satured $NH_4Cl$, and extracted with ether (4×200 ml). The combined ether phases were washed with NaCl, saturated solution, and dried ($MgSO_4$) and concentrated to yield a yellow oil in a white crystalline solid (phosphine oxide). The white solid was triturated with EtOAc and the mother liquor was purified by chromatography on an LPS-1 silica column. The fractions obtained were (A) [1S-[1β,2α(Z),3α,4β]]-7-[3-(2-oxo)ethyl-7-oxabicyclo[2.2.1-]hept-2yl]-5-heptenoic acid, methyl ester, (B) [1S-[1β,2α(Z),3α,4β]]-7-[3-(2-methoxy)ethenyl-7-oxabicyclo[2.2.1]hept-2-yl]-5-heptenoic acid, methyl ester, and (C) [1S-[1β,2α(Z),3α,4β]]-7-[3-(2,2-dimethoxy)ethyl-7-oxabicyclo[2.2.]-hept-2-yl]-5-heptonic acid, methyl ester.

Compounds (B) and (C) are each treated with trifluoroacetic acid to convert each to compound (A).

B.
[1S-[1β,2α(5Z),3α,4β]]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with $NaBH_4$ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated $KHCO_3$, saturated NaCl and dried ($MgSO_4$). The ether is evaporated to yield the title B compound.

C. [1S-[1β, 2α(Z),3α,4β]]-7-[3-[2-[[[(1-Oxohexyl)amino]acetyl]amino]ethyl]-7-oxabicyclo[2.2.1]hept-2-yl]-5-heptenoic acid Following the procedure of Examples 1 and 2 except substituting the above part B alcohol for the alcohol used in Example 1 Part B, the title compound is obtained.

D.
[1S-(1β,2α,3α,4β)]-7-[3-[2-[[[(1-Oxohexyl)amino]acetyl]amino]ethyl]-7-oxabicyclo[2.2.1]hept-2-yl]heptanoic acid Following the procedure of Part C and Example 1 except substituting [1S-(1β,2α,3α,4β)]-7-[3-formyl-7-oxabicyclo[2.2.1]hept-2-yl]heptanoic acid, methyl ester for [1S-[1β,2α(Z),3α,4β]]-7-[3-formyl-7-oxabicyclo[2.2.1]hept-2-yl]-5-heptenoic acid, methyl ester, the title compound is obtained.

E.
[-[1β,2α(5Z),3α,4β]]-1-Chloro-8-[[[(1-oxohexyl)amino]acetyl]amino]ethyl]-7-oxabicyclo[2.2.1]hept-2-yl]-6-octen-2-one Following the procedure of Example 1 Part F except substituting the above Part D acid for the Example 1 Part E acid, the title compound is obtained.

EXAMPLE 58

[1S-[1β,2α(5Z),3α,4β]]-1-Acetoxy-8-[3-[[[(1-oxohexyl)amino]acetyl]amino]ethyl]-7-oxabicyclo-[2.2.1]hept-2-yl]-6-octen-2-one Following the procedure of Example 2 except substituting the Example 57 compound for the Example 1 compound, the title compound is obtained

EXAMPLE 59

[1S-[1β,2α(5Z),3α,4β]]-1-Hydroxy-8-[3-[[[(1-oxohexyl)amino]acetyl]amino]ethyl]7-oxabicyclo[2.2.1]hept-2-yl]-6-octen-2-one Following the procedure of Example 3 except substituting the Example 58 compound for the Example 2 compound, the title compound is obtained.

EXAMPLE 60

[1S-[1β,2α(5Z),3α,4β]]-1-Hydroxy-8-[3-[2-[[[(1-oxopropyl)amino]acetyl]amino]ethyl]-7-oxabicyclo[2.2.1-]hept-2-yl]-6-octen-2-one Following the procedure of Example 57 to 59 except substituting propionoyl chloride for hexanoyl chloride, the title compound is obtained.

EXAMPLE 61

[1S-(1β,2α,3α,4β)]-7-[3-[2-[[[(1-Oxo-2-butenyl)-amino]acetyl]amino]ethyl]-7-oxabicyclo[2.2.1]-hept-2-yl]-2-octanone Following the procedure of Examples 57 to 59 and 32 to 34 except substituting 2-butenoyl chloride for hexanoyl chloride, the title compound is obtained.

EXAMPLE 62

[1S-[1β,2α(5Z),3α,4β]]-1-Hydroxy-8-[3-[2-[[[[(phenylamino)carbonyl]amino]acetyl]amino]ethyl]-7-oxabicyclo[2.2.1]hept-2-yl]-6-octen-2-one Following the procedure of Examples 57 to 59 and 4 to 6 except substituting phenyl isocyanate for n-butyl isocyanate, the title compound is obtained.

EXAMPLE 63

[1S-[1β,2α(5Z),3α,4β]]-Hydroxy-8-[3-[2-[[1-oxo-3-[ethyl(benzoyl)amino]propyl]amino]ethyl]-7-oxabicyclo[2.2.1]hept-2-yl]-6-octen-2-one Following the procedure of Examples 53 to 59 and 7 to 9 except substituting 3-(ethylamino)-propionic acid for sarcosine and benzoyl chloride for hexanoyl chloride, the title compound is obtained.

EXAMPLE 64

[1S-[1β,2α(5Z),3α,4β]]-7-[3-[4-[[[(1-Oxohexyl)amino]acetyl]amino]butyl]-7-oxabicyclo[2.2.1]-hept-2-yl]-6-octen-2-one

A.

[1S-[1β,2α(5Z),3α,4β]]-7-[3-(3-Oxo)-propyl-7-oxabicyclo[2.2.1]hept-2-yl]-5-heptenoic acid, methyl ester Following the procedure of Example 57 Part A except substituting [1S-[1β,2α(Z),3α,4β]]-7-[3-(2-oxo)-ethyl-7-oxabicyclo[2.2.1]hept-2-yl]-5-heptenoic acid, methyl ester for [1S-[1β,2α(Z),3α,4β]]-7-[3-formyl-7-oxabicyclo[2.2.1]hept-2-yl]-5-heptenoic acid, methyl ester, the title A compound is obtained,

B.

[1S-[1β,2α(Z),3α,4β]]-7-[3-(4-Oxo)-butyl-7-oxabicyclo[2.2.1]-hept-2-yl]-5-heptenoic acid, methyl ester Following the procedure of Example 53 Part A except substituting the aldehyde from Part A above for [1S-[1β,2α(Z),3α,4β]]-7-[3-formyl-7-oxabicyclo-[2.2.1]hept-2-yl]-5-heptenoic acid, methyl ester, the title B compound is obtained.

C.

[1S-[1β,2α(Z),3α,4β]]-7-[3-(4-Hydroxybutyl)-7-oxabicyclo[2.2.1]hept-2-yl]-5-heptenoic acid, methyl ester Following the procedure of Example 57 Part B except substituting the title B aldehyde for [1S-[1β,2α(Z)-,3α,4β]]-7-[3-(2-oxo)ethyl-7-oxabicyclo[2.2.1]hept-2-yl]-5-heptenoic acid, methyl ester, the title C alcohol is obtained.

D.

[1S-[1β,2α(Z),3α,4β]]-7-[3-[4-[[[(1-oxohexyl)amino]acetyl]amino]butyl]-7-oxabicyclo[2.2.1]hept-2-yl]-5-heptenoic acid Following the procedure of Examples 1 and 2 except substituting the above Part C alcohol for the alcohol used in Example 1, the title compound is obtained.

E.

[1S-[1β,2α(5Z),3α,4β]]-1-Chloro-8-[3-[4-[[[(1-oxohexyl)amino]acetyl]amino]butyl]-7-oxabicyclo[2.2.1]hept-2-yl]-6-octen-2-one Following the procedure of Example 1 Part F except substituting the above Part D acid for the Example 1 Part E acid, the title compound is obtained.

EXAMPLE 65

[1S-[1β,2α(5Z),3α,4β]-1-Acetoxy-8-[3-[4-[[[(1-oxohexyl)amino]acetyl]amino]-butyl]-7-oxabicyclo[2.2.1]hept-2-yl]-6-octen-2-one Following the procedure of Example 2 except substituting the Example 64 compound for the Example 1 compound, the title compound is obtained.

EXAMPLE 66

[1S-[1β,2α(5Z),3α,4β]-1-Hydroxy-8-[3-[4-[[[(1-oxohexyl)amino]acetyl]amino]butyl]-7-oxabicyclo-[2.2.1]hept-2-yl]-6-octen-2-one Following the procedure of Example 3 except substituting the Example 65 compound for the Example 2 compound, the title compound is obtained.

EXAMPLE 67

81S-[1β,2α(5Z),3α,4β]]-Chloro-9-[3-[[[[(1-oxohexyl)amino]acetyl]amino]methyl]-7-oxabicyclo-[2.2.1]hept-2yl]-6-nonen-2-one

A.

[1S-(1β,2α,3α,4β)]-3-[3-(Hydroxymethyl)-7-oxabicyclo[2.2.1]hept-2-yl]propionaldehyde A slurry of methoxymethyltriphenylphosphonium chloride (1.09 kg, 3.18 mol) in Burdick and Jackson sieve-dried tetrahydrofuran (3 liters) was chilled to 0° C. and treated dropwise with 1.4M potassium t-amylate in toluene (1910 ml, 2.67 mol) over 20 minutes. The resultant dark red solution was stirred at 0° C. for 1 hour. The mixture was then treated slowly over 5 minutes with solid hemiacetal (XVII in reaction sequence C) prepared as described in Example 3 of U.S. Pat. No. 4,143,054 (200 g, 1.28 mol). The temperature gradually rose to 23° C. The mixture was stirred vigorously at room temperature for 90 minutes. The reaction mixture was then chilled to 0° C. and treated slowly with acetaldehyde (124 ml, 2.2 mol) over 10 minutes. The mixture was diluted with water (2500 ml) and treated with 10% hydrochloric acid to pH 7. The mixture was then extracted with ether (7×2 liters). The combined ether extracts were dried over magnesium sulfate, filtered, and the filtrates concentrated in vacuo. The resultant mixture was treated with isopropyl ether (4 liters) and stirred overnight. The mixture was chilled to −10° C. for 90 minutes then filtered. The solids were washed thoroughly with isopropyl ether. The filtrate was concentrated in vacuo to an oily residue (460 g). This oily residue was treated with water (4000 ml) and stirred vigorously for 2 hours. The aqueous layer was decanted and the oily residue treated two additional times with water (2×1 liter). After the third wash, the residue solidified and was filtered. The combined aqueous triturates were concentrated in vacuo to 3.5 liters. The cloudy mixture was filtered through a bed of Celite. The filtrate was concentrated again to a volume of 2.3 liters. The cloudy solution was chilled in an ice bath and treated slowly with concentrated hydrochloric acid (683 ml). The mixture was then stirred at room temperature for 3 hours. After this time the solution was neutralized by the slow addition of solid sodium bicarbonate (720 g). The mixture was filtered through a bed of Celite then extracted with hexane (4×2 liters) then ethyl acetate (10×2 liters). The combined ethyl acetate extracts were dried over MgSO4 and concentrated in vacuo. The solid residue was triturated with hexane (1 liter), filtered, and dried in vacuo to yield 220 g (100%) of desired compound (hemiacetal F in reaction sequence C), m.p. 104°–105° C., [α]$_D$= +27° c=1 MeOH.

TLC: Silica gel; EtOAc; R$_f$=0.3; Ce(SO4)2.

The above Wittig procedure was repeated on the hemiacetal F used in place of hemiacetal XIII to form the title aldehyde.

B.

[1S-[1β,2α(Z),3α,4β]]-8-[3-(Hydroxymethyl)-7-oxabicyclo[2.2.1]hept-2-yl]-5-octenoic acid, methyl ester A Wittig reagent was prepared in dimethyl sulfoxide (dried over calcium hydride) by adding a solution of sodium methylsulfinylmethide (prepared by heating 600 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of Part A aldehyde 1.02 g (6 mmole) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gave an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 70 g of silica gel with 50/50 ethyl acetate-hexane as the eluant which gave 1.1 g of acid. This was treated with diazomethane ($CH_2N_2$) in $Et_2O$ to give the title compound.

C.

[1S-[1β,2α(Z),3α,4β]]-8-[3-[[[[(1-Oxohexyl)amino]acetyl]amino]methyl]-7-oxabicyclo[2.2.1]hept-2-yl]-5-octenoic acid Following the procedure of Examples 1 and 2 except substituting the title B ester for the ester used in Example 1 Part B, the title compound is obtained.

D.

[1S-[1β,2α(5Z),3α,4β]]-1-Chloro-9-[3-[[[[(1-oxohexyl)amino]acetyl]amino]methyl]-7-oxabicyclo[2.2.1]hept-2-yl]-6-nonen-2-one Following the procedure of Example 1 Part F except substituting the above Part C acid for the Example 1 Part E acid, the title compound is obtained.

EXAMPLE 68

[1S-[1β,2α(5Z),3α,4β]]-1-Acetoxy-9-[3-[[[[(1-oxohexyl)amino]acetyl]amino]methyl]-7-oxabicyclo[2.2.1]hept-2-yl]-6-nonen-2-one Following the procedure of Example 2 except substituting the Example 67 compound for the Example 1 compound, the title compound is obtained.

EXAMPLE 69

[1S-[1β,2α(5Z),3α,4β]]-1-Hydroxy-9-[3-[[[[(1-oxohexyl)amino]acetyl]amino]methyl]7-oxabicyclo[2.2.1]hept-2-yl]-6-nonen-2-one Following the procedure of Example 3 except substituting the Example 68 compound for the Example 2 compound, the title compound is obtained.

EXAMPLE 70

[1S-[1β,2α(6Z),3α,4β]]-1-Chloro-8-[3-[[[[(1-Oxohexyl)amino]acetyl]amino]methyl]-7-oxabicyclo-[2.2.1]hept-2-yl]-7-octen-2-one

A.

[1S-[1β,2α(6Z),3α,4β]]-7-[3-(Hydroxymethyl)-7-oxabicyclo[2.2.1]hept-2-yl]-heptenoic acid, methyl ester A slurry of carboxypentyl triphenylphosphonium bromide in THF is cooled in an ice bath and treated dropwise with 1.4M KOt-amylate in toluene. After completion of this addition, the reaction mixture is allowed to warm to room temperature and is stirred for 6 hours. To this stirred solution is then added a solution of hemiacetal XIII (reaction sequence G) (prepared as described in Example 3 of U.S. Pat. No. 4,143,054) in THF dropwise over 30 minutes. The reaction mixture is then stirred overnight (15 hours). The mixture is cooled in an ice bath and quenched with HOAc. The solvent is removed in vacuo and the resulting residue is dissolved in saturated NaCl solution. This is extracted with chloroform. The chloroform layers are then extracted with saturated $NaHCO_3$ solution. The aqueous extracts are acidified to pH~3.5 by addition of aqueous HCl solution, and then are extracted with several portions of chloroform. The combined chloroform extracts are concentrated in vacuo to afford the crude product. The crude acid is esterified with excess ethereal diazomethane at 0° C. and then is purified by chromatography on silica gel to afford the title ester.

B.

[1S-[1β,2α(6Z),3α,4β]]-7-[3-[[[[(1-Oxohexyl)amino]acetyl]amino]methyl]-7-oxabicyclo[2.2.1]hept-2-yl]-6-heptenoic acid Following the procedure of Example 1 except substituting the Part A ester for the hydroxymethyl compound used in Example 1 Part B, the title compound is obtained.

C.

[1S-[1β,2α(5Z),3α,4β]]-1-Chloro-8-[[[[(1-oxohexyl)amino]acetyl]amino methyl]-7oxabicyclo[2.2.1]hept-2-yl]-7-octen-2-one Following the procedure of Example 1 Part F except substituting the above Part D acid for the Example 1 Part E acid, the title compound is obtained.

EXAMPLE 71

[1S-[1β,2α(5Z),3α,4β]]-1-Acetoxy-8-[3-[[[[(1-oxohexyl)amino]acetyl]amino]methyl]-7-oxabicyclo[2.2.1]hept-2-yl]-7-octen-2-one Following the procedure of Example 2 except substituting the Example 70 compound for the Example 1 compound, the title compound is obtained

EXAMPLE 72

[1S-[1β,2α(5Z),3α,4β]]-1-Hydroxy-8-[3-[[[[(1-oxohexyl)amino]acetyl]amino]methyl]7-oxabicyclo[2.2.1]hept-2-yl]-7-octen -2-one Following the procedure of Example 3 except substituting the Example 71 compound for the Example 2 compound, the title compound is obtained.

EXAMPLE 73

[1S-[1β,2α(2E),3α,4β]]-1-Chloro-8-[3-[[[[(1-Oxohexyl)amino]acetyl]amino]methyl]-7-oxabicyclo-[2.2.1]hept-2-yl]-3-octen-2-one

A.
[1S-(1β,2α,3α,4β)]-5-[3-(Hydroxymethyl)-7-oxabicyclo[2.2.1]hept-2-yl]pentanal Following the procedure of Example 67 Part A, except substituting [1S-(1β,2α,3α,4β)]-3-[3-(hydroxymethyl)-7-oxabicyclo[2.2.1]hept-2-yl]-propionaldehyde for the hemiacetal XIII (see reaction sequence G or H), [1S-(1β,2α,3α,4β)]-4-[3-(hydroxymethyl)-7-oxabicyclo[2.2.1]hept-2-yl]-butanal is obtained. Then by repeating the procedure of Example 47 Part A on [1S-(1β,2α,3α,4β)]-4-[3-(hydroxymethyl)-7-oxabicyclo[2.2.1]hept-2-yl]butanal, the title A aldehyde is produced.

B.
[1S-[1β,2α(2E),3α,4β]]-7-[3-(Hydroxymethyl)-7-oxabicyclo[2.2.1]hept-2-yl]-2-heptenoic acid, methyl ester To a stirred solution of the title A aldehyde in MeOH is added carbomethoxymethylene triphenylphosphorane. The resulting solution is stirred under argon at room temperature for 24 hours. The solvent is then removed in vacuo and the resultant viscous oil is triturated with ether. The precipitated triphenylphosphine oxide is removed by filtration and the filtrate is concentrated in vacuo to afford a mixture of the (E) and (Z) esters. Purification is affected by chromatography to afford the pure title ester.

C.
[1S-[1β,2α(2E),3α,4β]]-7-[3-[[[[(1-Oxohexyl)amino]acetyl]amino]methyl]-7-oxabicyclo[2.2.1]hept-2-yl]-2-heptenoic acid Following the procedure of Example 1 except substituting the Part B ester for the ester used in Example 1 Part B, the title compound is obtained.

D.
[1S-[1β,2α(5Z),3α,4β]]-1-Chloro-8-[3-[[[[(1-oxohexyl)amino]acetyl]amino]methyl]-7-oxabicyclo[2.2.1]hept-2-yl]-3-octen-2-one Following the procedure of Example 1 Part F except substituting the above Part C acid for the Example 1 Part E acid, the title compound is obtained.

EXAMPLE 74

[1S-[1β,2α(5Z),3α,4β]]-1-Acetoxy-8-[3-[[[[(1-oxohexyl)amino]acetyl]amino]methyl]-7-oxabicyclo[2.2.1]hept-2-yl]-3-octen-2-one Following the procedure of Example 2 except substituting the Example 73 compound for the Example 1 compound, the title compound is obtained.

EXAMPLE 75

[1S-[1β,2α(5Z),3α,4β]]-1-Hydroxy-8-[3-[[[[(1-oxohexyl)amino]acetyl]amino]methyl]-7-oxabicyclo[2.2.1]hept-2-yl]-3-octen-2-one [

Following the procedure of Example 3 except substituting the Example 74 compound for the Example 2 compound, the title compound is obtained.

EXAMPLE 76

[1S-[1β,2α(5Z),3α,4β]]-7-[3-[(Methylamino)methyl]-7-oxabicyclo[2.2.1]hept-2-yl]-5-heptenoic acid, methyl ester Chiral amine from Example 1, Part C, (1 mmole) and N,N-dimethylformamide dimethylacetal (1.5 mmole) are dissolved in $CH_2Cl_2$ (6 ml). The reaction is stirred at room temperature overnight. The solvent and the excess reagent are evaporated to give crude amidine, which is dissolved in $CH_2Cl_2$ (5 ml). Methyl triflate (2 mmole) is added into the reaction at room temperature and the reaction is stirred for 1 hour at room temperature. The organic solvent and the excess reagent are evaporated off in vacuo and the residue is treated with methanolic hydrogen chloride at room temperature overnight. The reaction is concentrated in vacuo and the resulting crude product is dissolved in 1N HCl. The water layer is washed with ethyl ether and basified with saturated $NaHCO_3$. The water layer is extracted with ethyl ether, which is dried over $MgSO_4$. Filtration and evaporation of the solvent leave a crude product, which is purified by silica gel column to give the title compound.

The title compound is then employed in place of the chiral amine from Example 1 Part C to prepare compounds of the invention wherein $R^1$ is $CH_3$.

EXAMPLES 77 to 104

Following the procedures outlined in the specification and described in the above working Examples, the following compounds may be prepared.

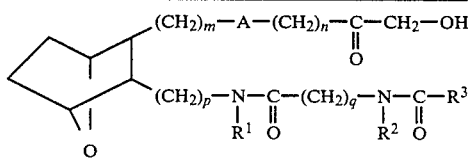

| Ex. No. | m | A | $(CH_2)_n$ | p | $R^1$ | $(CH_2)_q$ | $R^2$ | $R^3$ |
|---|---|---|---|---|---|---|---|---|
| 77. | 2 | CH=CH | $CH_2$ | 1 | H | $(CH_2)_2$ | $CH_3$ | H |
| 78. | 3 | $(CH_2)_2$ | $(CH_2)_2$ | 2 | $C_2H_5$ | $(CH_2)_3$ | H | $CH_3$ |
| 79. | 4 | CH=CH | $(CH_2)_3$ | 3 | H | $(CH_2)_4$ | H | —CH=CH—$CH_3$ |
| 80. | 1 | $(CH_2)_2$ | $(CH_2)_4$ | 1 | $CH_3$ | $(CH_2)_5$ | $CH_3$ | —C≡C—$CH_3$ |
| 81. | 0 | CH=CH | $(CH_2)_5$ | 2 | H | $(CH_2)_6$ | $C_2H_5$ | —$CH_2$—C≡C—$CH_3$ |
| 82. | 2 | CH=CH | $CH_3$<br>\|<br>—CH— | 3 | $C_2H_5$ | $(CH_2)_7$ | $C_3H_7$ | H  H<br>\|  \|<br>—$CH_2$—C=C—$CH_3$— |

-continued

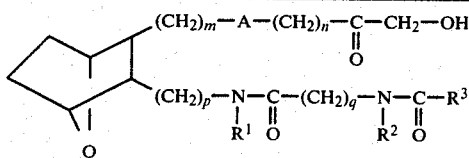

| Ex. No. | m | A | $(CH_2)_n$ | p | $R^1$ | $(CH_2)_q$ | $R^2$ | $R^3$ |
|---|---|---|---|---|---|---|---|---|
| 83. | 3 | $(CH_2)_2$ | $-\overset{CH_3}{\underset{CH_3}{C}}-$ | 4 | H | $-\overset{CH_3}{CH}-$ | $C_4H_9$ | $C_6H_5$ |
| 84. | 4 | $(CH_2)_2$ | $(CH_2)_4$ | 1 | $C_3H_7$ | $-CH_2-$ | $C_5H_{11}$ | $C_6H_5$ |
| 85. | 1 | CH=CH | $-\overset{CH_3}{\underset{}{C}}-CH_2-\overset{CH_3}{}$ | 2 | H | $-CH_2-\overset{CH_3}{CH}-$ | H | $CH_2C_6H_5$ |
| 86. | 0 | CH=CH | $-\overset{CH_3}{CH}-\overset{CH_3}{CH}-$ | 3 | $CH_3$ | $-CH_2-\overset{CH_3}{\underset{}{C}}-\overset{CH_3}{}$ | H | $-(CH_2)_2C_6H_5$ |
| 87. | 1 | $(CH_2)_2$ | $-\overset{CH_3}{\underset{F}{C}}-CH_2-$ | 4 | $C_2H_5$ | $-CH_2-\overset{CH_3}{CH}-CH_2-$ | H | $-C_6H_4-p-CH_3$ |
| 88. | 2 | CH=CH | $-\overset{F}{CH}-\overset{F}{CH}-$ | 1 | H | $-(CH_2)_3-$ | $CH_3$ | $-C_6H_4-p-OH$ |
| 89. | 3 | $(CH_2)_2$ | $-\overset{F}{\underset{}{C}}-CH_2-\overset{F}{}$ | 2 | $C_4H_9$ | $-CH_2-\overset{C_2H_5}{CH}-$ | $CH_3$ | $-OCH_3$ |
| 90. | 4 | $(CH_2)_2$ | $-(CH_2)_5$ | 3 | H | $-CH_2-\overset{CH_3}{\underset{H}{C}}-CH_2-$ | $CH_3$ | $-OC_2H_5$ |
| 91. | 0 | CH=CH | $-CH_2-\overset{CH_3}{CH}-CH_2-$ | 4 | $CH_2$ | $-\overset{CH_3}{\underset{CH_3}{C}}-CH_2-$ | $C_2H_5$ | $-OC_6H_5$ |
| 92. | 0 | $(CH_2)_2$ | $-CH_2-\overset{CH_3}{\underset{}{C}}-\overset{CH_3}{}$ | 1 | $C_2H_5$ | $(CH_2)_2$ | $CH_3$ | $-NH_2$ |
| 93. | 1 | CH=CH | $CH_2$ | 2 | $C_2H_5$ | $C_2H_5$ | H | $-NHCH_3$ |
| 94. | 2 | $(CH_2)_2$ | $(CH_2)_2$ | 3 | $CH_3$ | $-CH_2-\overset{CH_3}{\underset{CH_3}{C}}-$ | $C_4H_9$ | $-NHC_6H_5$ |
| 95. | 3 | CH=CH | $(CH_2)_3$ | 4 | $C_2H_5$ | $-CH_2-\overset{CH_3}{CH}-\overset{CH_3}{CH}-CH_2-$ | $CH_3$ | $NCH_3(C_2H_5)$ |
| 96. | 4 | $(CH_2)_2$ | $(CH_2)_4$ | 1 | $C_3H_7$ | $(CH_2)_2$ | $C_2H_5$ | $-N(CH_3)_2$ |
| 97. | 0 | CH=CH | $-\overset{F}{\underset{}{CH_2C}}-\overset{F}{}$ | 2 | $C_4H_9$ | $(CH_2)_3$ | $CH_3$ | H |
| 98. | 1 | $(CH_2)_2$ | $-CH_2-\overset{CH_3}{\underset{}{C}}-\overset{CH_3}{}$ | 3 | $C_5H_{11}$ | $-\overset{F}{CH}-CH_2-$ | $C_3H_7$ | $C_4H_9$ |
| 99. | 2 | CH=CH | $(CH_2)_5$ | 4 | H | $-\overset{F}{\underset{}{C}}-CH_2\overset{F}{}$ | $CH_4H_9$ | $-(CH_2)_2CH=CHCH_3$ |

-continued

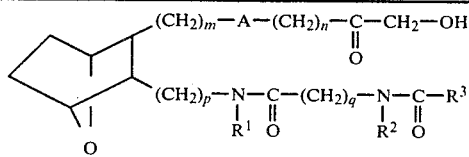

| Ex. No. | m | A | (CH₂)ₙ | p | R¹ | (CH₂)q | R² | R³ |
|---|---|---|---|---|---|---|---|---|
| 100. | 3 | (CH₂)₂ | —CH₂—CH(CH₃)(F)— | 1 | H | (CH₂)₂ | H | C₆H₅ |
| 101. | 4 | (CH₂)₂ | (CH₂)₂ | 2 | H | CH₂ | H | —CH₂C₆H₅ |
| 102. | 0 | CH=CH | (CH₂)₃ | 3 | CH₃ | (CH₂)₃ | C₃H₇ | —OC₄H₉ |
| 103. | 2 | (CH₂)₂ | (CH₂)₄ | 4 | CH₃ | (CH₂)₈ | H | —OC₆H₅ |
| 104. | 3 | CH=CH | (CH₂)₅ | 1 | CH₃ | (CH₂)₁₀ | H | —NCH₃(C₆H₅) |

What is claimed is:

1. A compound having the structure

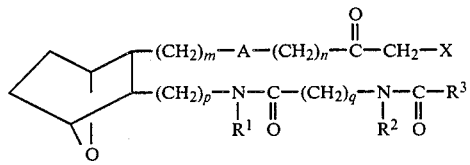

including all stereoisomers thereof, wherein m is 0 to 4; A is —CH=CH— or —CH₂—CH₂—; n is 1 to 5; X is halogen, alkanoyloxy or hydroxyl; p is 1 to 4; R¹ is H or lower alkyl; q is 1 to 12; R² is H or lower alkyl; and R³ is H, lower alkyl, lower alkenyl containing 2 to 12 carbons, lower alkynyl containing 2 to 12 carbons, aryl, arylalkyl, lower alkoxy, aryloxy, amino, alkylamino, or arylamino, wherein lower alkyl or alkyl alone or as part of another group contains 1 to 12 carbons and is unsubstituted or is substituted with halo, CF₃, alkoxy, aryl, alkyl-aryl, haloaryl, cycloalkyl, alkylcycloalkyl, hydroxy, alkylamino, alkanoylamino, arylcarbonylamino, nitro, cyano, thiol or alkylthio;

aryl alone or as part of another group contains 6 to 10 carbons in the ring portion and is unsubstituted or is substituted with 1 or 2 lower alkyl groups, 1 or 2 halogens, 1 or 2 hydroxy groups, 1 or 2 lower alkoxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups;

cycloalkyl alone or as part of another group contains 3 to 12 carbons and is unsubstituted or is substituted with 1 or 2 halogens, 1 or 2 lower alkyl groups, 1 or 2 lower alkoxy groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups; (CH₂)ₘ, (CH₂)ₙ and (CH₂)ₚ may contain 1 or 2 lower alkyl and/or 1 or 2 halo substituents; and (CH₂)q may contain one or more halo, hydroxy, alkoxy, amino, alkylamino, arylamino, amido, thioamido, thiol, alkylthio, arylthio, cyano or nitro groups.

2. The compound as defined in claim 1 wherein X is halogen.

3. The compound as defined in claim 1 wherein X is lower alkanoyloxy.

4. The compound as defined in claim 1 wherein X is hydroxyl.

5. The compund as defined in claim 1 where in R³ is lower alkyl or lower alkoxy.

6. The compound as defined in claim 1 wherein A is CH=CH.

7. The compound as defined in claim 1 wherein m is 1 and n is 1 to 4.

8. The compound as defined in claim 1 wherein p is 1 and q is 1.

9. The compound as defined in claim 1 wherein R¹ is H and R² is H or CH₃.

10. The compound as defined in claim 1 wherein m is 1, n is 2 to 4, p is 1, R¹ is H, q is 1, R² is H or lower alkyl and R³ is lower alkyl or lower alkoxy.

11. The compound as defined in claim 1 having the name [1S-[1β,2α(5Z),3α,4β]]-1-chloro-8-[3-[[[[(1-oxohexyl)amino]acetyl]amino]methyl]-7-oxabicyclo[2.2.1]hept-2-yl]-6-octen-2-one or esters thereof, including all stereoisomers thereof.

12. The compound as defined in claim 1 having the name [1S-[1β,2α(5Z),3α,4β]]-1-acetoxy-8-[3-[[[[(1-oxohexyl)amino]acetyl]amino]methyl]-7-oxabicyclo[2.2.1]hept-2-yl]-6-octen-2-one, including all stereoisomers thereof.

13. The compound as defined in claim 1 having the name [1S-[1β,2α(5Z),3α,4β]]-1-hydroxy-8-[3-[[[[(1-oxohexyl)amino]acetyl]amino]methyl]-7-oxabicyclo[2.2.1]hept-2-yl]-6-octen-2-one, including all stereoisomers thereof.

14. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

15. The method as defined in claim 14 wherein said compound is administered in an amount within the range of from about 1 to about 100 mg/kg.

16. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

17. A method of inhibiting platelet aggregation or inhibiting bronchoconstriction associated with asthma, which comprises administering to a mammalian host an effective amount of a compound as defined in claim 1 or a pharmaceutically acceptable salt thereof.

18. A method of treating peripheral vascular diseases, which comprises topically or systemically administering to a mammalian host an effective amount of a compound as defined in claim 1 or a pharmaceutically acceptable salt thereof.

* * * * *